(12) United States Patent
Shiozawa et al.

(10) Patent No.: US 7,306,908 B2
(45) Date of Patent: Dec. 11, 2007

(54) NUCLEIC ACIDS ASSOCIATED WITH RHEUMATOID ARTHRITIS, AND METHODS AND KITS FOR THE DIAGNOSIS THEREOF

(75) Inventors: Shunichi Shiozawa, Kobe (JP); Yoshitake Konishi, Shinjuku-ku (JP)

(73) Assignee: Shunichi Shiozawa, Hyogo (JP)

( * ) Notice: Subject to any disclaimer, the term of this patent is extended or adjusted under 35 U.S.C. 154(b) by 468 days.

(21) Appl. No.: 10/415,247

(22) PCT Filed: Oct. 24, 2001

(86) PCT No.: PCT/JP01/09313

§ 371 (c)(1), (2), (4) Date: Apr. 24, 2003

(87) PCT Pub. No.: WO02/34912

PCT Pub. Date: May 2, 2002

(65) Prior Publication Data

US 2004/0013655 A1    Jan. 22, 2004

(30) Foreign Application Priority Data

Oct. 24, 2000 (JP) ............................ 2000-324296
Mar. 27, 2001 (JP) ............................ 2001-090546
Mar. 30, 2001 (JP) ............................ 2001-099990

(51) Int. Cl.
C12Q 1/68    (2006.01)
C07H 21/02    (2006.01)
C07H 21/04    (2006.01)

(52) U.S. Cl. .................. 435/6; 536/23.1; 536/23.5; 536/24.31

(58) Field of Classification Search .............. None
See application file for complete search history.

(56) References Cited

FOREIGN PATENT DOCUMENTS

| EP | 1 008 648 A1 | 6/2000 |
|---|---|---|
| WO | WO 96/20213 | 7/1996 |
| WO | WO 97/33904 | 9/1997 |
| WO | WO 98/51791 | 11/1998 |
| WO | WO 01/32921 A2 | 5/2001 |

OTHER PUBLICATIONS

Mahairas et al. NCBI Database, National Library of Medicine, NIH (Bethesda, MD, USA) GenBank Accession No. AQ070468, Aug. 5, 1998.*
Mahairas et al . Proceedings of the National Academies of Sciences, USA. 1999. 96: 9739-9744.*
Screaton et al . Proceedings of the National Academies of Sciences, USA. 1997. 94: 4615-4619.*
Perkin Elmer Cetus Catalog. 1988. GenAmp™ DNA Amplification Reagent Kit.*
Database EMBL EBI; "Homo sapiens DR3 gene, mutant DR3 sequence", XP002290055, retrieved from EBI Database accession No. AB051851, (2001).

U.S. Appl. No. 10/501,259, filed Jul. 9, 2004, Shiozawa et al.
Shiozawa, Shunichi, et al., Shikkan Idenshi kara mita Mansei Kansetsu Rheumatism (RA) no Byoutai to Chiryou, *Nippon Seikei Geka Gakkai Zasshi*, Feb. 25, 2001, vol. 75, No. 2, p. S15.
Murayama, Kouichi, et al., Mansei Kansetsu Rheumatism (RA) no Shikkan Idenshi Death Receptor 3 (DR3) Heni no Doutei, *Rheumatism*, Apr. 17, 2001, vol. 41, No. 2, p. 509.
Shiozawa, Shunichi, et al., Mansei Kansetsu Rheumatism (RA) no Shikkan Idenshi, *Rheumatism* Apr. 17, 2001, vol. 41, No. 2, p. 335.
Shiozawa, Shunichi, et al., Mansei Kansetsu Rheumatism to Shikkan Idenshi, *Saishin Igaku*, Apr. 10, 2001, vol. 56, No. 4, pp. 833-844.
Shiozawa, Shunichi, et al., Mansei Kansetsu Rheumatism to Shikkan Idenshi, Aug. 31, 2001, vol. 41, No. 4, pp. 763-772.
Shiozawa, S., et al., An Approach to Identify New Genes in Autoimmune Diseases: Lessons From Rheumatoid Arthritis, *Reviews in Immunogenetics*. vol. 2, pp. 133-139, (2000).
Ishikawa, Hitoshi, How to Achieve the Diagnosis of Rheumatoid Arthritis *Treatment*, vol. 73, No. 3, pp. 23-27, Mar. 1991.
Harris, Jr., Edward D., Rheumatoid Arthritis Pathophysiology and Implications for Therapy, *The New England Journal of Medicine*, vol. 322, No. 18, pp. 1277-1289.
Vyse, Timothy J.; et al., Genetic Analysis of Autoimmune Disease, *Cell*, vol. 85, pp. 311-318, May 3, 1996.
Nakajima, Toshihiro, et al., Apoptosis and Functional Fas Antigen in Rheumatoid Arthritis Synoviocytes, *Arthritis & Rheumatism*, vol. 38, No. 4, pp. 485-491, Apr. 1995.
Fujisawa Koushi, et al., Therapeutic Effect of the Anti-Fas Antibody on Arthritis in HTLV-1 tax Transgenic Mice, *J. Clin. Invest.*, vol. 98, No. 2 pp. 271-278, Jul. 1996.
Sakai, Kiyoshi, et al., Potential Withdrawal of Rheumatoid Synovium By The Induction of Apoptosis Using A Novel in Vivo Model Of Rheumatoid Arthritis, *Arthritis & Rheumatism*, vol. 41, No. 7, pp. 1251-1257, Jul. 1998.
Mukae.N, et al., The Measurement of the Death Receptor 3 (DR3) Expression in mRNA of RA Patent's Peripheral Blood Mononuclear Cells, Rheumatism, vol. 39, No. 2, pp. 444-445 (1999); and Konishi, Y., et al., Search for Gene with Relation to the Disease Sensitivity to Rheumatoid Arthritis (RA), Rheumatism, vol. 39, No. 2, pp. 444-445, (1999).

(Continued)

*Primary Examiner*—Carla J. Myers
(74) *Attorney, Agent, or Firm*—Edwards Angell Palmer & Dodge LLP; David G. Conlin; Mark D. Russett

(57) ABSTRACT

Mutations in a genome associating in rheumatoid arthritis (RA) are found in human DR3 genomic DNA having the base sequence represented by SEQ ID NO:1. The invention provides a genome having such mutations, transcripts thereof, a method of highly accurately evaluating the RA onset or the RA onset possibility by using the mutations thereof, an evaluation kit therefor, and a therapeutic method and remedies for RA.

4 Claims, 5 Drawing Sheets

OTHER PUBLICATIONS

Bodmer, Jean-Luc, et al., TRAMP, a Novel apoptosis-Mediating Receptor with Sequence Homology to Tumor Necrosis Factor Receptor 1 and Fas(Apo-1/CD95), *Immunity*, vol. 6, pp. 79-88, Jan. 1997.

Marsters, Scot A., et al., Identification of a Ligand for theDdeath-domain-containingRreceptor Apo3, *Current Biology*, vol. 8, No. 9, pp. 525-528, Apr. 13, 1998.

* cited by examiner lane 1 : 100bp ladder
lane 2-4 : PCR products amplified from genome having a mutation
lane 5 : PCR products amplified from a normal genome mutation   —   all

SEQUENCE LISTING

<160> NUMBER OF SEQ ID NOS: 21

<210> SEQ ID NO 1
<211> LENGTH: 4825
<212> TYPE: DNA
<213> ORGANISM: Homo sapiens
<220> FEATURE:
<221> NAME/KEY: intron
<222> LOCATION: (128)..(635)
<220> FEATURE:

-continued

```
<221> NAME/KEY: intron
<222> LOCATION: (757)..(973)
<220> FEATURE:
<221> NAME/KEY: intron
<222> LOCATION: (1109)..(1476)
<220> FEATURE:
<221> NAME/KEY: intron
<222> LOCATION: (1645)..(1742)
<220> FEATURE:
<221> NAME/KEY: intron
<222> LOCATION: (1822)..(3068)
<220> FEATURE:
<221> NAME/KEY: intron
<222> LOCATION: (3125)..(3225)
<220> FEATURE:
<221> NAME/KEY: intron
<222> LOCATION: (3334)..(3529)
<220> FEATURE:
<221> NAME/KEY: intron
<222> LOCATION: (3578)..(4021)
<220> FEATURE:
<221> NAME/KEY: intron
<222> LOCATION: (4203)..(4433)

<400> SEQUENCE: 1
cgggccctgc gggcgcgggg ctgaaggcgg aaccacgacg ggcagagagc acggagccgg      60
gaagcccctg ggcgcccgtc ggagggctat ggagcagcgg ccgcggggct gcgcggcggt     120
ggcggcggtg agttgagacg caggaggcta ggggcagctt tgagccctgt cccaagagcc     180
tcggtgaagg aaggggcccc gggcgcgtct ccactccaag cctcactggg ggctgggttg     240
gccgcccttt ccgatctcgt taaaggctcc tccaggcgt agcccttcca ctgagaggaa      300
acccctccca ggagggtctg ggggcccag gcagagcatt atcagtgtcc ctcccccaac      360
agaaagcatg ggtgggggtg ggggcgctgc tggattcctg ctctggtgga ggggaaactt     420 gtgagggct ggtaagcgcc ccctccgaag cctggtgtgt gcgcggggg aaggaagtta       480 gtttcctctc cacccatggg cacccctcct gcccggggcc tgggaagtgg gctgctctgt     540
gggcaaatgc tggggcctct gaaatggagg agacgcagca gggagaggcc ccacgtgggc     600
agctgcgctg agagtcagca gcacctgtcc cccaggcgct cctcctggtg ctgctggggg     660
cccgggccca gggcggcact cgtagcccca ggtgtgactg tgccggtgac ttccacaaga     720
agattggtct gttttgttgc agaggctgcc cagcgggtaa gtggccacag gggtgggaga     780
ggcatggggc aggcagggct ggagaggtgg cgggcaggcc cgggaggtaa gaggaggctg     840
gcaggggagg taggggtagg ctgacagaga agtagggagc tggagagaaa gagggaggga     900
gggcagggtg ggaagcaggt cggggggttgc tgggcagccc ctctgcctgc ctgaccctg     960 cctggttcca cagggcacta cctgaaggcc ccttgcacgg agccctgcgg caactccacc    1020
tgccttgtgt gtcccaaga caccttcttg gcctgggaga accaccataa ttctgaatgt     1080
gcccgctgcc aggcctgtga tgagcagggt gaggggcttc tcagtgcttg cagggagtt    1140 cctaaggaca ggccttttctg aaggaagtgg ctggctcggg cccaaacttg gggtgtgagg    1200
gtcctgcacc caccccttgcc agaaccctcc accctgatcc tccttcaggg tgcccttgcc    1260
ccttctctct tcctggtgac cttcccatct ctccatgtgc cttggcctct ggtcggcctt    1320
aatctctgag cttctctctt ttttagggta gccctgtacc tgtctgtctt tcgcctattt    1380
ctgtctccat tatcttggga taatgcctct gcctctccat gggagccttt ggccctgact    1440
aactctccac tccccatctc cctgcacccc caccagcctc ccaggtggcg ctggagaact    1500
gttcagcagt ggccgacacc cgctgtggct gtaagccagg ctggtttgtg gagtgccagg    1560
tcagccaatg tgtcagcagt tcacccttct actgccaacc atgcctagac tgcggggccc    1620
```

-continued

```
tgcaccgcca cacacggcta ctctgtgagt accccaccc agggctctct actcccagac   1680
cccttctcc ctgcctgacc cactcctgtc ccatggtgac gcatgcctct cctggattgc   1740
aggttcccgc agagatactg actgtgggac ctgcctgcct ggcttctatg aacatggcga   1800
tggctgcgtg tcctgcccca cgtaattcct agctgtcgtg ggatggaggg aagggcggct   1860
gggagcagag caggggcctg gggtggggca ggtgctgctg gttcaggaat aggaagaggg   1920
gatagggagg agggagcctt ggccctgtga tgggtgggcc ccacttcagg caaacttaga   1980
tggcaaaaga gcaatctgga tccgccttag ccagatacat aagggtattt gccttcactt   2040
tcagccagca ttcccccag cgatcctagc cagatattac agatgatttg tcacttacac   2100
agagagtcac attgatatag ctttaaaact tgggctgaag gaggttgagg ctgcagtgag   2160
ctatgatcgt gccactgcac ttcagcctgg gcaacagagc gagacctatt aaataaataa   2220
ataaatatta aatctattaa atattaaata ttaaatctat taaataaata aatacaaagg   2280
gctgagagtc aggactgtgc tgctagttct ctaggggatc ttgggcaagt gcagagaatt   2340
cgcgtctctg atgtgtggtg tccctttctc aacatgggat gttagcagct aattcacagg   2400
cctttgatca gaggtaaggg actttctgta gctattcaag tcttttttt ttttttttt   2460
tttttttt gagatggaga cttgctctgt cacccaggct ggagtgcagt ggcacgatct   2520
tggctcacta caacctctgc tgcctgggtt caagtgattc tcctgcctca gcctcccaag   2580
tagctgggac tacaggagcc caccaccacc cccggctaat tttttgtatt tttagtagag   2640
acggggtttc accgtgttag ccaagatggt cttgatcacc tgacctcgtg atccaccgc    2700
cttggcctcc caaagtgctg ggattacagg catgagccac cgcgcccggc ctccattcaa   2760
gtctttattg aatatctgct atgttctaca cactgttcta ggtgctgggg atgcaacagg   2820
ggacaaaata ggcaaaatcc ctgtcctttt ggggttgaca ttctagtgac tcttcatgta   2880
gtctagaaga agctcagtga atagtgtctg tggttgttac cagggacaca atgacaggaa   2940
cattcttggg tagagtgaga ggcctgggga gggaagggtc tctaggatgg agcagatgct   3000
gggcagtctt agggagcccc tcctggcatg caccccctca tccctcaggc cacccccgtc   3060
ccttgcagga gcaccctggg gagctgtcca gagcgctgtg ccgctgtctg tggctggagg   3120
cagagtaggt ggtgtgctgg gaatgcgagt gggagaactg ggatggaccg aggggaggcg   3180
ggtgaggagg ggggcaacca cccaacaccc accagctgct ttcagtgttc tgggtccagg   3240
tgctcctggc tggccttgtg gtcccctcc tgcttgggc cacctgacc tacacatacc    3300
gccactgctg gcctcacaag cccctggtta ctggtaagta cacacaccca cacgcacc     3360
cagaagcctg gggtcaggat gggtagccca gagtctactc aaccctgata cagaagggga   3420
aactgaggca gggagtgtgg ggtgcagagg aaccctagag gagctgtacc agcacccagg   3480
tccaggaggc ttgcctggtg gctgaccgca atctctctgt gtctgtcagc agatgaagct   3540
gggatggagg ctctgacccc accaccggta agaacctcac tgtgtgattc tgggctgcct   3600
tctggagctg gaagatcaag ccttactatg atccctggag cttggcacgc ggccagcacc   3660
gggtagccct agtggacaga ggtgttggga gcagagtcat cagtggatga gaccagcaca   3720
gtgcctgccc tcaaggggtg ctcagtcagc tggagttcag attcgtacac aggagctaac   3780
agttcaatgg aaggagagcc ccatggtgct ggggacaag aggaaggagg cggggcagg    3840
ggactcaagg cagaagcaag agttctgctg gctacagtg agagcagggc caactgtggg   3900
aggtgtcatt gcgggggtgt ctgctgactg aaccaggac tgtcccctcc tggagaggca   3960
```

-continued

```
ctgcgggtaa ggggccttac ttggcaagca gggctgacct ggggcccctc ttggcttcca      4020
ggccacccat ctgtcaccct tggacagcgc ccacacccct ctagcacctc ctgacagcag      4080
tgagaagatc tgcaccgtcc agttggtggg taacagctgg accctgggct accccgagac      4140
ccaggaggcg ctctgcccgc aggtgacatg gtcctgggac cagttgccca gcagagctct      4200
tggtaaggga catcagtggc ctgaggcctt gaccccattc tcctgtctgc ggtgggaagt      4260
tgtggtttca caacgtgttc cctttctgcc ccctaactga cggagtccgc cctatgccct      4320
gacccaccgg atccagcggg cttcagcccc ggggtacccg cacgaacgcc cctgactctg      4380
cctcccgacc gcggcccacg tacccccaatt ggctctctct ggccctgccc caggccccgc      4440
tgctgcgccc acactctcgc cagagtcccc agccggctcg ccagccatga tgctgcagcc      4500
gggcccgcag ctctacgacg tgatggacgc ggtcccagcg cggcgctgga aggagttcgt      4560
gcgcacgctg gggctgcgcg aggcagagat cgaagccgtg gaggtggaga tcggccgctt      4620
ccgagaccag cagtacgaga tgctcaagcg ctggcgccag cagcagcccg cgggcctcgg      4680
agccgtttac gcggccctgg agcgcatggg gctggacggc tgcgtggaag acttgcgcag      4740
ccgcctgcag cgcggccccgt gacacggcgc ccacttgcca cctaggcgct ctggtggccc      4800
ttgcagaagc cctaagtacg gttac                                           4825
```

<210> SEQ ID NO 2
<211> LENGTH: 1634
<212> TYPE: DNA
<213> ORGANISM: Homo sapiens
<220> FEATURE:
<221> NAME/KEY: CDS
<222> LOCATION: (89)..(1342)

<400> SEQUENCE: 2

```
cgggccctgc gggcgcgggg ctgaaggcgg aaccacgacg ggcagagagc acggagccgg       60
gaagcccctg ggcgcccgtc ggagggct atg gag cag cgg ccg cgg ggc tgc        112
                                 Met Glu Gln Arg Pro Arg Gly Cys
                                  1               5 gcg gcg gtg gcg gcg gcg ctc ctc ctg gtg ctg ctg ggg gcc cgg gcc        160
Ala Ala Val Ala Ala Ala Leu Leu Leu Val Leu Leu Gly Ala Arg Ala
             10                  15                  20 cag ggc ggc act cgt agc ccc agg tgt gac tgt gcc ggt gac ttc cac        208
Gln Gly Gly Thr Arg Ser Pro Arg Cys Asp Cys Ala Gly Asp Phe His
     25                  30                  35                  40 aag aag att ggt ctg ttt tgt tgc aga ggc tgc cca gcg ggg cac tac        256
Lys Lys Ile Gly Leu Phe Cys Cys Arg Gly Cys Pro Ala Gly His Tyr
                 45                  50                  55 ctg aag gcc cct tgc acg gag ccc tgc ggc aac tcc acc tgc ctt gtg        304
Leu Lys Ala Pro Cys Thr Glu Pro Cys Gly Asn Ser Thr Cys Leu Val
             60                  65                  70 tgt ccc caa gac acc ttc ttg gcc tgg gag aac cac cat aat tct gaa        352
Cys Pro Gln Asp Thr Phe Leu Ala Trp Glu Asn His His Asn Ser Glu
         75                  80                  85 tgt gcc cgc tgc cag gcc tgt gat gag cag gcc tcc cag gtg gcg ctg        400
Cys Ala Arg Cys Gln Ala Cys Asp Glu Gln Ala Ser Gln Val Ala Leu
         90                  95                 100 gag aac tgt tca gca gtg gcc gac acc cgc tgt ggc tgt aag cca ggc        448
Glu Asn Cys Ser Ala Val Ala Asp Thr Arg Cys Gly Cys Lys Pro Gly
105                 110                 115                 120 tgg ttt gtg gag tgc cag gtc agc caa tgt gtc agc agt tca ccc ttc        496
Trp Phe Val Glu Cys Gln Val Ser Gln Cys Val Ser Ser Ser Pro Phe
                125                 130                 135
```

```
tac tgc caa cca tgc cta gac tgc ggg gcc ctg cac cgc cac aca cgg      544
Tyr Cys Gln Pro Cys Leu Asp Cys Gly Ala Leu His Arg His Thr Arg
            140                 145                 150 cta ctc tgt tcc cgc aga gat act gac tgt ggg acc tgc ctg cct ggc      592
Leu Leu Cys Ser Arg Arg Asp Thr Asp Cys Gly Thr Cys Leu Pro Gly
            155                 160                 165 ttc tat gaa cat ggc gat ggc tgc gtg tcc tgc ccc acg agc acc ctg      640
Phe Tyr Glu His Gly Asp Gly Cys Val Ser Cys Pro Thr Ser Thr Leu
        170                 175                 180 ggg agc tgt cca gag cgc tgt gcc gct gtc tgt ggc tgg agg cag atg      688
Gly Ser Cys Pro Glu Arg Cys Ala Ala Val Cys Gly Trp Arg Gln Met
185                 190                 195                 200 ttc tgg gtc cag gtg ctc ctg gct ggc ctt gtg gtc ccc ctc ctg ctt      736
Phe Trp Val Gln Val Leu Leu Ala Gly Leu Val Val Pro Leu Leu Leu
                205                 210                 215 ggg gcc acc ctg acc tac aca tac cgc cac tgc tgg cct cac aag ccc      784
Gly Ala Thr Leu Thr Tyr Thr Tyr Arg His Cys Trp Pro His Lys Pro
            220                 225                 230 ctg gtt act gca gat gaa gct ggg atg gag gct ctg acc cca cca ccg      832
Leu Val Thr Ala Asp Glu Ala Gly Met Glu Ala Leu Thr Pro Pro Pro
            235                 240                 245 gcc acc cat ctg tca ccc ttg gac agc gcc cac acc ctt cta gca cct      880
Ala Thr His Leu Ser Pro Leu Asp Ser Ala His Thr Leu Leu Ala Pro
        250                 255                 260 cct gac agc agt gag aag atc tgc acc gtc cag ttg gtg ggt aac agc      928
Pro Asp Ser Ser Glu Lys Ile Cys Thr Val Gln Leu Val Gly Asn Ser
265                 270                 275                 280 tgg acc cct ggc tac ccc gag acc cag gag gcg ctc tgc ccg cag gtg      976
Trp Thr Pro Gly Tyr Pro Glu Thr Gln Glu Ala Leu Cys Pro Gln Val
                285                 290                 295 aca tgg tcc tgg gac cag ttg ccc agc aga gct ctt ggc ccc gct gct     1024
Thr Trp Ser Trp Asp Gln Leu Pro Ser Arg Ala Leu Gly Pro Ala Ala
            300                 305                 310 gcg ccc aca ctc tcg cca gag tcc cca gcc ggc tcg cca gcc atg atg     1072
Ala Pro Thr Leu Ser Pro Glu Ser Pro Ala Gly Ser Pro Ala Met Met
            315                 320                 325 ctg cag ccg ggc ccg cag ctc tac gac gtg atg gac gcg gtc cca gcg     1120
Leu Gln Pro Gly Pro Gln Leu Tyr Asp Val Met Asp Ala Val Pro Ala
        330                 335                 340 cgg cgc tgg aag gag ttc gtg cgc acg ctg ggg ctg cgc gag gca gag     1168
Arg Arg Trp Lys Glu Phe Val Arg Thr Leu Gly Leu Arg Glu Ala Glu
345                 350                 355                 360 atc gaa gcc gtg gag gtg gag atc ggc cgc ttc cga gac cag cag tac     1216
Ile Glu Ala Val Glu Val Glu Ile Gly Arg Phe Arg Asp Gln Gln Tyr
                365                 370                 375 gag atg ctc aag cgc tgg cgc cag cag cag ccc gcg ggc ctc gga gcc     1264
Glu Met Leu Lys Arg Trp Arg Gln Gln Gln Pro Ala Gly Leu Gly Ala
            380                 385                 390 gtt tac gcg gcc ctg gag cgc atg ggg ctg gac ggc tgc gtg gaa gac     1312
Val Tyr Ala Ala Leu Glu Arg Met Gly Leu Asp Gly Cys Val Glu Asp
            395                 400                 405 ttg cgc agc cgc ctg cag cgc ggc ccg tga cacggcgccc acttgccacc       1362
Leu Arg Ser Arg Leu Gln Arg Gly Pro
        410                 415 taggcgctct ggtggccctt gcagaagccc taagtacggt tacttatgcg tgtagacatt  1422
ttatgtcact tattaagccg ctggcacggc cctgcgtagc agcaccagcc ggccccaccc  1482
ctgctcgccc ctatcgctcc agccaaggcg aagaagcacg aacgaatgtc gagaggggt   1542 gaagacattt ctcaacttct cggccggagt ttggctgaga tcgcggtatt aaatctgtga  1602
```
aagaaaacaa aaaaaaaaaa aaaaaaaaaa aa                    1634

<210> SEQ ID NO 3
<211> LENGTH: 417
<212> TYPE: PRT
<213> ORGANISM: Homo sapiens

<400> SEQUENCE: 3

```
Met Glu Gln Arg Pro Arg Gly Cys Ala Ala Val Ala Ala Leu Leu
  1               5                  10                  15

Leu Val Leu Leu Gly Ala Arg Ala Gln Gly Gly Thr Arg Ser Pro Arg
                 20                  25                  30

Cys Asp Cys Ala Gly Asp Phe His Lys Lys Ile Gly Leu Phe Cys Cys
             35                  40                  45

Arg Gly Cys Pro Ala Gly His Tyr Leu Lys Ala Pro Cys Thr Glu Pro
         50                  55                  60

Cys Gly Asn Ser Thr Cys Leu Val Cys Pro Gln Asp Thr Phe Leu Ala
 65                  70                  75                  80

Trp Glu Asn His His Asn Ser Glu Cys Ala Arg Cys Gln Ala Cys Asp
                 85                  90                  95

Glu Gln Ala Ser Gln Val Ala Leu Glu Asn Cys Ser Ala Val Ala Asp
            100                 105                 110

Thr Arg Cys Gly Cys Lys Pro Gly Trp Phe Val Glu Cys Gln Val Ser
        115                 120                 125

Gln Cys Val Ser Ser Ser Pro Phe Tyr Cys Gln Pro Cys Leu Asp Cys
    130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
                165                 170                 175

Val Ser Cys Pro Thr Ser Thr Leu Gly Ser Cys Pro Glu Arg Cys Ala
            180                 185                 190

Ala Val Cys Gly Trp Arg Gln Met Phe Trp Val Gln Val Leu Leu Ala
        195                 200                 205

Gly Leu Val Val Pro Leu Leu Leu Gly Ala Thr Leu Thr Tyr Thr Tyr
    210                 215                 220

Arg His Cys Trp Pro His Lys Pro Leu Val Thr Ala Asp Glu Ala Gly
225                 230                 235                 240

Met Glu Ala Leu Thr Pro Pro Ala Thr His Leu Ser Pro Leu Asp
                245                 250                 255

Ser Ala His Thr Leu Leu Ala Pro Pro Asp Ser Ser Glu Lys Ile Cys
                260                 265                 270

Thr Val Gln Leu Val Gly Asn Ser Trp Thr Pro Gly Tyr Pro Glu Thr
            275                 280                 285

Gln Glu Ala Leu Cys Pro Gln Val Thr Trp Ser Trp Asp Gln Leu Pro
        290                 295                 300

Ser Arg Ala Leu Gly Pro Ala Ala Ala Pro Thr Leu Ser Pro Glu Ser
305                 310                 315                 320

Pro Ala Gly Ser Pro Ala Met Met Leu Gln Pro Gly Pro Gln Leu Tyr
                325                 330                 335

Asp Val Met Asp Ala Val Pro Ala Arg Arg Trp Lys Glu Phe Val Arg
            340                 345                 350

Thr Leu Gly Leu Arg Glu Ala Glu Ile Glu Ala Val Glu Val Glu Ile
        355                 360                 365
```

```
Gly Arg Phe Arg Asp Gln Gln Tyr Glu Met Leu Lys Arg Trp Arg Gln
    370                 375                 380
Gln Gln Pro Ala Gly Leu Gly Ala Val Tyr Ala Ala Leu Glu Arg Met
385                 390                 395                 400
Gly Leu Asp Gly Cys Val Glu Asp Leu Arg Ser Arg Leu Gln Arg Gly
                405                 410                 415
Pro

<210> SEQ ID NO 4
<211> LENGTH: 787
<212> TYPE: DNA
<213> ORGANISM: Homo sapiens
<220> FEATURE:
<221> NAME/KEY: CDS
<222> LOCATION: (89)..(655)

<400> SEQUENCE: 4
cgggccctgc gggcgcgggg ctgaaggcgg aaccacgacg gcagagagc acggagccgg      60 gaagcccctg gcgcccgtc ggagggct atg gag cag cgg ccg cgg ggc tgc       112
                              Met Glu Gln Arg Pro Arg Gly Cys
                                1               5 gcg gcg gtg gcg gcg gcg ctc ctc ctg gtg ctg ctg ggg gcc cgg gcc     160
Ala Ala Val Ala Ala Ala Leu Leu Leu Val Leu Leu Gly Ala Arg Ala
         10                  15                  20 cag ggc ggc act cgt agc ccc agg tgt gac tgt gcc ggt gac ttc cac     208
Gln Gly Gly Thr Arg Ser Pro Arg Cys Asp Cys Ala Gly Asp Phe His
 25                  30                  35                  40 aag aag att ggt ctg ttt tgt tgc aga ggc tgc cca gcg ggg cac tac     256
Lys Lys Ile Gly Leu Phe Cys Cys Arg Gly Cys Pro Ala Gly His Tyr
                 45                  50                  55 ctg aag gcc cct tgc acg gag ccc tgc ggc aac tcc acc tgc ctt gtg     304
Leu Lys Ala Pro Cys Thr Glu Pro Cys Gly Asn Ser Thr Cys Leu Val
             60                  65                  70 tgt ccc caa gac acc ttc ttg gcc tgg gag aac cac cat aat tct gaa     352
Cys Pro Gln Asp Thr Phe Leu Ala Trp Glu Asn His His Asn Ser Glu
         75                  80                  85 tgt gcc cgc tgc cag gcc tgt gat gag cag gcc tcc cag gtg gcg ctg     400
Cys Ala Arg Cys Gln Ala Cys Asp Glu Gln Ala Ser Gln Val Ala Leu
     90                  95                 100 gag aac tgt tca gca gtg gcc gac acc cgc tgt ggc tgt aag cca ggc     448
Glu Asn Cys Ser Ala Val Ala Asp Thr Arg Cys Gly Cys Lys Pro Gly
105                 110                 115                 120 tgg ttt gtg gag tgc cag gtc agc caa tgt gtc agc agt tca ccc ttc     496
Trp Phe Val Glu Cys Gln Val Ser Gln Cys Val Ser Ser Ser Pro Phe
                125                 130                 135 tac tgc caa cca tgc cta gac tgc ggg gcc ctg cac cgc cac aca cgg     544
Tyr Cys Gln Pro Cys Leu Asp Cys Gly Ala Leu His Arg His Thr Arg
            140                 145                 150 cta ctc tgt tcc cgc aga gat act gac tgt ggg acc tgc ctg cct ggc     592
Leu Leu Cys Ser Arg Arg Asp Thr Asp Cys Gly Thr Cys Leu Pro Gly
        155                 160                 165 ttc tat gaa cat ggc gat ggc tgc gtg tcc tgc ccc act aga gac ggg     640
Phe Tyr Glu His Gly Asp Gly Cys Val Ser Cys Pro Thr Arg Asp Gly
    170                 175                 180 gtt tca ccg tgt tag ccaagatggt cttgatcacc tgacctcgtg atccacccgc     695
Val Ser Pro Cys
185 cttggcctcc caaagtgctg ggattacagg catgagccac cgcgcccggc ctccattcaa    755
```
gtctttattg aatatctgct atgttctaca ca            787

<210> SEQ ID NO 5
<211> LENGTH: 188
<212> TYPE: PRT
<213> ORGANISM: Homo sapiens

<400> SEQUENCE: 5

Met Glu Gln Arg Pro Arg Gly Cys Ala Ala Val Ala Ala Leu Leu
 1               5                  10                  15

Leu Val Leu Leu Gly Ala Arg Ala Gln Gly Gly Thr Arg Ser Pro Arg
            20                  25                  30

Cys Asp Cys Ala Gly Asp Phe His Lys Lys Ile Gly Leu Phe Cys Cys
        35                  40                  45

Arg Gly Cys Pro Ala Gly His Tyr Leu Lys Ala Pro Cys Thr Glu Pro
    50                  55                  60

Cys Gly Asn Ser Thr Cys Leu Val Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
            100                 105                 110

Thr Arg Cys Gly Cys Lys Pro Gly Trp Phe Val Glu Cys Gln Val Ser
        115                 120                 125

Gln Cys Val Ser Ser Ser Pro Phe Tyr Cys Gln Pro Cys Leu Asp Cys
    130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
                165                 170                 175

Val Ser Cys Pro Thr Arg Asp Gly Val Ser Pro Cys
            180                 185

<210> SEQ ID NO 6
<211> LENGTH: 47
<212> TYPE: DNA
<213> ORGANISM: Artificial sequence
<220> FEATURE:
<223> OTHER INFORMATION: Synthesized oligonucleotide

<400> SEQUENCE: 6
ggggtaccat ccgcttcctg ccccagccag gctggtttgt ggagtgc            47

<210> SEQ ID NO 7
<211> LENGTH: 49
<212> TYPE: DNA
<213> ORGANISM: Artificial sequence
<220> FEATURE:
<223> OTHER INFORMATION: Synthesized oligonucleotide

<400> SEQUENCE: 7
ccgctcgagg ggccacctcc agtgccagtg gcggtatgtg taggtcagg            49

<210> SEQ ID NO 8
<211> LENGTH: 16
<212> TYPE: DNA
<213> ORGANISM: Artificial sequence
<220> FEATURE:
<223> OTHER INFORMATION: Synthesized oligonucleotide

<400> SEQUENCE: 8

```
atccgcttcc tgcccc                                                   16

<210> SEQ ID NO 9
<211> LENGTH: 18
<212> TYPE: DNA
<213> ORGANISM: Artificial sequence
<220> FEATURE:
<223> OTHER INFORMATION: Synthesized oligonucleotide

<400> SEQUENCE: 9
ggggccacct ccagtgcc                                                 18

<210> SEQ ID NO 10
<211> LENGTH: 28
<212> TYPE: DNA
<213> ORGANISM: Artificial sequence
<220> FEATURE:
<223> OTHER INFORMATION: Synthesized oligonucleotide

<400> SEQUENCE: 10
ggttcccgca gaggtactga ctgtggga                                      28

<210> SEQ ID NO 11
<211> LENGTH: 28
<212> TYPE: DNA
<213> ORGANISM: Artificial sequence
<220> FEATURE:
<223> OTHER INFORMATION: Synthesized oligonucleotide

<400> SEQUENCE: 11
tcccacagtc agtacctctg cgggaacc                                      28

<210> SEQ ID NO 12
<211> LENGTH: 30
<212> TYPE: DNA
<213> ORGANISM: Artificial sequence
<220> FEATURE:
<223> OTHER INFORMATION: Synthesized oligonucleotide

<400> SEQUENCE: 12
cttggctcac tataacctct gctgcctggg                                    30

<210> SEQ ID NO 13
<211> LENGTH: 30
<212> TYPE: DNA
<213> ORGANISM: Artificial sequence
<220> FEATURE:
<223> OTHER INFORMATION: Synthesized oligonucleotide

<400> SEQUENCE: 13
cccaggcagc agaggttata gtgagccaag                                    30

<210> SEQ ID NO 14
<211> LENGTH: 30
<212> TYPE: DNA
<213> ORGANISM: Artificial sequence
<220> FEATURE:
<223> OTHER INFORMATION: Synthesized oligonucleotide

<400> SEQUENCE: 14
gatggtcttg atctcctgac ctcgtgatcc                                    30

<210> SEQ ID NO 15
<211> LENGTH: 30
<212> TYPE: DNA
```

<213> ORGANISM: Artificial sequence
<220> FEATURE:
<223> OTHER INFORMATION: Synthesized oligonucleotide

<400> SEQUENCE: 15
ggatcacgag gtcaggagat caagaccatc                                           30

<210> SEQ ID NO 16
<211> LENGTH: 31
<212> TYPE: DNA
<213> ORGANISM: Artificial sequence
<220> FEATURE:
<223> OTHER INFORMATION: Synthesized oligonucleotide

<400> SEQUENCE: 16
gcaacagggg acagaatagg caaaatccct g                                         31

<210> SEQ ID NO 17
<211> LENGTH: 31
<212> TYPE: DNA
<213> ORGANISM: Artificial sequence
<220> FEATURE:
<223> OTHER INFORMATION: Synthesized oligonucleotide

<400> SEQUENCE: 17
cagggatttt gcctattctg tccctgttg c                                          31

<210> SEQ ID NO 18
<211> LENGTH: 28
<212> TYPE: DNA
<213> ORGANISM: Artificial sequence
<220> FEATURE:
<223> OTHER INFORMATION: Synthesized oligonucleotide

<400> SEQUENCE: 18
tgttcccgca gaggtactga ctgtggga                                             28

<210> SEQ ID NO 19
<211> LENGTH: 28
<212> TYPE: DNA
<213> ORGANISM: Artificial sequence
<220> FEATURE:
<223> OTHER INFORMATION: Synthesized oligonucleotide

<400> SEQUENCE: 19
tcccacagtc agtacctctg cgggaaca                                             28

<210> SEQ ID NO 20
<211> LENGTH: 18
<212> TYPE: DNA
<213> ORGANISM: Artificial sequence
<220> FEATURE:
<223> OTHER INFORMATION: Synthesized oligonucleotide

<400> SEQUENCE: 20
cgaggcggcc aggaggtg                                                        18

<210> SEQ ID NO 21
<211> LENGTH: 20
<212> TYPE: DNA
<213> ORGANISM: Artificial sequence
<220> FEATURE:
<223> OTHER INFORMATION: Synthesized oligonucleotide

```
<400> SEQUENCE: 21
ggttcagcaa tagccgcaga                                              20
```

NUCLEIC ACIDS ASSOCIATED WITH RHEUMATOID ARTHRITIS, AND METHODS AND KITS FOR THE DIAGNOSIS THEREOF

TECHNICAL FIELDS

The present invention relates to genomes having mutations, a diagnosis method of human rheumatoid arthritis by using transcripts of the genomes and the mutation of the genomes, a method of evaluating the onset possibility thereof, and a diagnostic kit for detecting the genomes. More specifically, the present invention relates to a therapeutic method and remedies for rheumatoid arthritis.

BACKGROUND OF THE INVENTION

Rheumatoid arthritis (hereinafter also referred to as "RA") mainly produces a symptom of multiple erosive arthritis, and rheumatoid arthritis is also unidentified systemic inflammatory disease affecting multiple organs. RA develops chronically while alternating between remission and exacerbation, causes the damage and deformation of joints if left untreated, and finally shows the dysfunction of motor organs. In some cases, RA is life-threatening. Therefore, RA patients suffer physically and mentally from heavy pain all their lives.

RA shows a wide variety of symptoms. For the diagnosis of RA, the diagnostic criteria by the American College of Rheumatology have been widely used. However, the RA onset is slow and usually takes several weeks to several months. The percentage positive of a rheumatoid factor, which is used as an objective index in the diagnostic criteria adopted by the American College of Rheumatology, is about 33% within three months and about 88% in twelve months and longer (Treatment, Vol. 73, No. 3, pp 23-27, in 1991), and a definite diagnosis of RA has not been achieved. Consequently, approaches to the diagnosis of rheumatoid arthritis have been made by detecting rheumatoid arthritis-associated IgM antibodies in patient sera that react with a recombinant antigen (See Japanese Laid-Open Patent Publication No. 513257/1998 (Tokukaihei 10-513257)).

Further, in the therapy for RA, therapeutic measures to be selected usually differ depending on a progressing course in the condition of RA pathema. Generally, in an early stage when a definite diagnosis cannot be given, non-steroidal anti-inflammatory drug (NSAID) is administered. In the case when the definite diagnosis can be given, disease modifying anti-rheumatic drugs (DMARD) is administered in addition to NSAID. Especially in the early stage of the RA onset, a definite diagnosis is difficult to be given. Under the present circumstances, discrimination from other rheumatoid diseases including collagen disease is carried out together with a careful observation of the progress while NSAID is administered. When symptoms progress further, steroid drug may be administered, and a medical therapy for the enhancement of pain relief is carried out together with a physical therapy and an orthotic therapy for the maintenance and recovery of joint function. Furthermore, when the joint damage causes inconvenience in a daily life, a surgical therapy may be carried out.

Aspects of arthritis and joint damage causing RA, particularly the pathological courses thereof, have been elucidated gradually through various research works. RA is induced by the concomitant participation of numerous causative factors including living environment and is then exacerbated progressively to the stage of apparent diseases; therefore, the interactive mechanism per se of such numerous factors should be elucidated for accurate characterization and appropriate therapeutic management of the disease. The prevalence of RA is not more than 1% on a global scale (New England Journal of Medicine, Vol. 322, p. 1277-1289, in 1990), but the frequency of the disease is about 8 times greater in the siblings of the patients with the disease (Cell, Vol. 85, p. 311-318, in 1996). Hence, it is predicted that a certain genetic factor may serve as one of the causative factors. Since an environment is regarded as one of the causative factors, previous knowledge of the RA onset possibility makes it possible to delay and prevent the RA onset by attentions to the diet, virus infection, stresses, etc. in daily life. Furthermore, an early diagnosis and a proper treatment in early stages can delay the course of RA and expect the improvement of prognosis.

One of immediate causes of RA is excessive inhibition of apoptosis. Regarding this, the following facts have been reported. In synovial cells of RA patients, apoptosis is induced in vitro by anti-Fas antibody (Arthritis and Rheumatism, Vol. 38, p. 485-491, in 1995). Further, administration of anti-Fas antibody to a human T-cell leukemia virus type I (HTLV-I) tax transgenic mouse as a model animal of RA inhibits edema of joints and arthritis (Journal of Clinical Investigation, Vol. 98, p. 271-278, in 1996); moreover, synovial cells of RA transplanted to the dorsum of a SCID mouse disappears by administration of anti-Fas antibody (Arthritis and Rheumatism, Vol. 41, p. 1251-1257, in 1998).

In International Patent Publication WO98/51791, the inventors of the present application have conducted the linkage analysis using microsatellite markers to RA patients and their siblings and specified three loci where causative genes of rheumatoid arthritis are located. The following causative genes have been identified:

(1) A causative gene of rheumatoid arthritis, which gene is located within ±1 centimorgan on a DNA sequence on human chromosome 1 to which the microsatellite markers D1S214 and/or D1S253 are hybridized.

(2) A causative gene of rheumatoid arthritis, which gene is located within ±1 centimorgan on a DNA sequence on human chromosome 8 to which the microsatellite marker D8S556 is hybridized.

(3) A causative gene of rheumatoid arthritis, which gene is located within ±1 centimorgan on a DNA sequence on human chromosome X to which the microsatellite markers DXS1001, DXS1047, DXS1205, DXS1227 and/or DXS1232 are hybridized.

Further, in Rheumatism, No. 39, No. 2, p. 444-445, the inventors of the present application have indicated death receptor 3 (hereinafter also referred to as "DR3"), which relates to the causative gene (1) with the markers D1S214 and D1S253, confirmed restriction fragment length polymorphism of DR3 between healthy subjects and RA patients, and suggested the possibility that DR3 may be the gene with relation to the disease sensitivity to RA.

An object of the present invention is to elucidate the relation between mutations of a genome in human DR3 and the RA onset or the RA onset possibility, and to provide a method of highly accurately diagnosing the RA onset or the RA onset possibility by using the mutations thereof. Another object of the present invention is to provide a diagnostic kit useful for detecting a genome having the mutations in DR3 responsible for RA or transcripts thereof. Still another object of the present invention is to provide a therapeutic method and remedies effective for the RA patients having the mutations in DR3.

DISCLOSURE OF THE INVENTION

In such circumstances, as a result of extensive research, in the cells obtained from test subjects, the inventors of the present application found a genome having the following mutations in SEQ ID No:1 of the DR3 genome:

(1) A cytosine (C) to thymine (T) substitution of a base at position 921;

(2) An adenine (A) to guanine (G) substitution of a base at position 1755;

(3) A deletion of bases at positions 2443 to 2456;

(4) A cytosine (C) to thymine (T) substitution of a base at position 2531;

(5) An adenine (A) to thymine (T) substitution of a base at position 2678, and (6) An adenine (A) to guanine (G) substitution of a base at position 2826.

Further, the adenine (A) to guanine (G) substitution of the base at position 1755, which exists in the region of an exon of the DR3 genome, means a mutation from aspartic acid to glycine in the amino acid at position 159 of a DR3 protein whose amino acid sequence is represented by SEQ ID NO:3. Meanwhile, the mutations (1) and (3) through (6) exist in the regions of introns of the DR3 genome.

Conventionally, it has been known that a plurality of genomes are responsible for the RA onset, and the mutant genome of the present invention constitutes a partial cause of the RA onset.

With such knowledge, the present invention was completed by finding that useful are a method of evaluating the RA onset or the RA onset possibility (in other words, a method of diagnosis of RA) using a mutant DR3 genome of the cells obtained from the test subjects and transcripts thereof as an index, and a diagnostic kit for detecting the mutation. Furthermore, the present invention is useful in providing a new prevention method, therapeutic method, and remedies for rheumatoid arthritis. The following will specifically describe the present invention.

In the present specification, A, C, G, and T represent bases of adenine, cytosine, guanine, and thymine, respectively, unless otherwise stated. Further, amino acids and amino acid residues are expressed by a one-letter code or three-letter code defined by IUPAC or IUB. Still further, the transcripts are products generated as a result of the transcription and translation of the genome; for example, mRNA, cDNA, and proteins are named.

The base at position 1755 corresponds to the 564th base of the cDNA sequence (Accession No. NM_003790) registered in the GeneBank. The deletion at positions 2443 to 2456 corresponds to the deletion of bases from positions 622 to 635 with respect to the 3'-end of Exon 5 of the genomic DNA, when the base at this end of Exon 5 is used as a reference and the adjacent base of the following Intron is the first position. Further, the mutations at positions 2531, 2678, and 2826 correspond to the bases at positions −538, −391, and −243, respectively, when the base at the 5'-end of Exon 6 is used as a reference and the adjacent base of the preceding intron is position −1 (see FIG. 1). Note that, in the region where T exists in successive 28 bases (at positions 2443 to 2470), the number of the bases may increase or decrease by three bases. Also, in the region where T of the mutant genome exists in successive 14 bases, the number of the bases may also increase or decrease by three bases.

The method of evaluating the RA onset or the RA onset possibility (in other words, a method of the diagnosis of RA) and the evaluation kit (in other words, a diagnostic kit of RA) are adapted to use the genome and transcripts thereof, such as mRNA and cDNA. For example, mRNA can be used by converting it into cDNA. The genome is useful as a probe for evaluating the RA onset or the RA onset possibility. Further, genomic fragments containing at least one of the mutations are also useful as probes.

Further, in transcripts such as proteins expressed from the genome, the mutations can also be detected. Such transcripts of the genome are also useful as a reagent for evaluating the RA onset or the RA onset possibility or a material thereof.

(a) Use of Genome

The present invention, using the genome, can identify the mutant genome and diagnose RA (i.e. the evaluation of the RA onset or the RA onset possibility) as follows, for example.

The genomes of test subjects can be obtained from any cells of the human body by a common procedure. For example, the genomes can be obtained from hairs, organs, peripheral lymphocytes, synovial cells, etc. The genomes can be also obtained from the cells that were cultured to proliferate. Further, the obtained genomes can be used by amplifying them by common genetic amplification methods such as the PCR (Polymerase Chain Reaction) method, NASBA (Nucleic Acid Sequence Based Amplification) method, TMA (Transcription-Mediated Amplification) method, and SDA (Strand Displacement Amplification) method.

Detection methods of genomic mutations are not especially limited. As the methods, named are, for example, the allyl specific oligonucleotide probe method, Oligonucleotide Ligation Assay method, PCR-SSCP method, PCR-CFLP method, PCR-PHFA method, invader method, RCA (Rolling Circle Amplification) method, Primer Oligo Base Extension method.

The base sequence at positions 21 to 4825 of SEQ ID NO:1 can be determined, for example, by direct sequencing of the PCR products amplified from the genome by the following primer combinations (1 to 3). Note that, the base sequence at positions 1 to 20 of SEQ ID NO:1 is the cDNA sequence (Accession No. NM_003790) registered in the GeneBank.

1: Sense primer at positions 21 to 38 of SEQ ID NO:1 and antisense primer at positions 1517 to 1535 of SEQ ID NO:1

2: Sense primer at positions 1051 to 1078 of SEQ ID NO:1 and antisense primer at positions 4058 to 4085 of SEQ ID NO:1

3: Sense primer at positions 4023 to 4043 of SEQ ID NO:1 and antisense primer at positions 4809 to 4825 of SEQ ID NO:1

The mutations used in the present invention: A to G substitution of the base at position 1755 of SEQ ID NO:1; C to T substitution of the base at position 2531 of SEQ ID NO:1; A to T substitution of the base at position 2678 of SEQ ID NO:1, and A to G substitution of the base at position 2826 of SEQ ID NO:1 can be detected by direct sequencing of the PCR products amplified by the sense primer at positions 1051 to 1078 of SEQ ID NO:1 and the antisense primer at positions 4058 to 4085 of SEQ ID NO:1. Further, the deletion of the bases at positions 2443 to 2456 of SEQ ID NO:1 can be detected. In other words, in the case where the above mutations of five bases simultaneously occur, it is possible to detect them from the PCR products simultaneously.

Moreover, the C to T substitution of the base at position 921 of SEQ ID NO:1 can be detected by sequencing of the PCR products amplified by the sense primer at positions 21 to 38 of SEQ ID NO:1 and the antisense primer at positions 1517 to 1535 of SEQ ID NO:1.

Namely, the mutations can be detected by direct sequencing of the PCR products amplified from the genome by prepared a sense primer and an antisense primer for the region where the mutations are included. By detecting at least one of the mutations in the genome of SEQ ID NO:1, the RA diagnosis (the evaluation of the RA onset or the RA onset possibility) of the test subjects can be performed at high accuracy.

The primers used in the present invention can be prepared by apparatuses such as a DNA synthesizer by a common procedure.

Alternately, using an appropriate restriction enzyme, such mutations can be detected by detecting the difference in size between the digested genomic fragments by a method such as Southern blotting.

Among the above mutations, the deletion of the bases at positions 2443 to 2456 of SEQ ID NO:1 can be detected by subcloning the PCR products into plasmids and sequencing them, or by detecting the difference in size between the PCR products amplified by the sense primer at positions 2369 to 2389 of SEQ ID NO:1 and the PCR products amplified by the antisense primer at positions 2514 to 2535 of SEQ ID NO:1.

(b) Use of Transcripts

In the present invention, the RA diagnosis of the test subjects (the evaluation of the RA onset or the RA onset possibility) can be performed at a high accuracy by detecting transcripts such as mRNA and proteins having variations caused by the genomic mutations.

For example, in the case where mRNA is used as a transcript, it is possible to detect the mutations by recombining the sequence containing the mutations, for example, positions 1534 to 3306 on the SEQ ID NO:1, into an expression vector, which is transfected into a cell, and by comparing mRNAs derived from the vector. The mutations can also be detected by preparing cDNA from mRNA and sequencing the cDNA.

More specifically, mRNA holding the positions 2636 to 2792 of SEQ ID NO:1 is detected from the vector having the following mutations: the A to G substitution of the base at position 1755 of SEQ ID NO:1, the deletion of the bases at positions 2443 to 2456 of SEQ ID NO:1, the C to T substitution of the base at position 2531 of SEQ ID NO:1, the A to T substitution of the base at position 2678 of SEQ ID NO:1, and the A to G substitution of the base at position 2826 of SEQ ID NO:1. A part of the base sequence of the mRNA is SEQ ID NO:4, and the insertion of introns generates a frame shift, which changes the amino acid residues and a terminator codon appears. The amino acid sequence of the protein expressed from this mRNA is represented by SEQ ID NO:5.

Further, mRNAs derived from the vectors that were respectively transfected in cells are compared, the vectors being, for example, (1) an expression vector into which positions 1534 to 3306 of SEQ ID NO:1 are recombined, (2) the expression vector of (1) into which an A to G mutation is introduced at position 1755 of SEQ ID NO:1, (3) the expression vector of (1) into which a C to T mutation is introduced at position 2531 of SEQ ID NO:1, (4) the expression vector of (1) into which an A to T mutation is introduced at position 2678 of SEQ ID NO:1, and (5) the expression vector of (1) into which an A to G mutation is introduced at position 2826 of SEQ ID NO:1.

As a result, in only the vector into which the A to T mutation was introduced at position 2678 of SEQ ID NO:1, mRNA holding positions 2636 to 2792 of SEQ ID NO:1 were amplified, whereby it is confirmed that this mutation causes abnormal splicing, and it is possible to detect the mutation.

In the case where proteins are used as transcripts, for example, proteins can be detected by the following methods: a method of detecting a protein having a mutation, from Asp to Gly, of the amino acid residue at position 159 in the amino acid sequence of SEQ ID NO:2, a method of detecting a protein, represented by SEQ ID NO:5, which results from the foregoing abnormal splicing of mRNA, and a method of detecting a protein having a mutation from Asp to Gly, of the amino acid residue at position 159 in the amino acid sequence of SEQ ID NO:5. Preferably, proteins are detected by a method of detecting a protein having a mutation from Asp to Gly, of the amino acid residue at position 159 in the amino acid sequence of SEQ ID NO:2. The detection of the mutant protein may be based on a common protein-sequencing method. For example, named are the following methods: a method of preparing an antibody that recognizes only a mutant protein and detecting by the ELISA method, a method of isolating a protein, cutting by an enzyme, etc., either directly or optionally, and detecting the mutation using a protein sequencer, a method of detecting the mutation at the isoelectric point of the amino acid, and a method of detecting a difference in mass by mass spectrometry. A preferable method is the method of preparing an antibody they recognizes only a mutant protein and detecting by the ELISA method.

Meanwhile, one of the immediate causes of RA is excessive inhibition of apoptosis. The apoptosis is caused, for example, in the following steps.

A death factor (for example, Fas ligand, TNF, Apo3L (DR3 liqand), and TRIAL are named) binds to a death receptor (Fas, TNF receptor, and DR3 are named), to which an adapter protein (for example, FADD and TRADD) then binds before causing apoptosis by the intervention of a caspase molecular group.

For example, caspase-8 binds to the death receptor via an adaptor protein in response to a stimulus and becomes activated. The activated caspase-8 activates other enzymes, such as caspase-3 in the downstream of the cascade and finally causes apoptosis. Further, it is known that caspase-8 has variants such as caspase-8/a and caspase-8/b.

The protein which is expressed from the genome detected in the present invention has mutations caused by aberrant splicing. Because of these mutations, a mutant DR3 is expressed in which a death domain region is deleted. It has been known that DR3 is a trimer, and the adaptor protein binds to the death domain region of the trimer. This mutant receptor also forms a complex together with a normal receptor; however, TRADD, which is an adaptor protein, cannot bind to this complex. As a result, the caspase-8 cannot be activated, and apoptosis cannot be activated.

Therefore, it is considered that the mutant DR3 induced from the genome having the mutations detected in the present invention is not functional and is dominant negative.

For example, these can be confirmed by the following steps (1) to (4).

(1) Obtaining Cells from Test Subjects

The cells used for diagnosis can be obtained from any cells of the human body by a common procedure. For example, the cells can be obtained from peripheral lymphocytes, synovial cells, organs, etc. The cells may be suitably incubated to proliferate before they are used.

The cells are preferably peripheral-blood mononuclear cells.

(2) Stimulation of Cells

The cells are stimulated by a reagent or the like. The reagent used for the stimulation is not specially limited, provided that it is used for usual stimulation purposes. Examples of the reagents include: ligands of death receptor such as Fas ligand, TNF, and DR3 ligand; anti-Fas antibody; actinomycin D; radiation; glucocorticoid; phorbol 12-myristate 13-acetate (PMA), and phytohemagglutinin (PHA). These reagents may be used in a combination of one or more kinds. Further, DR3 ligand, PMA, and PHA are preferable. (Incidentally, stimulation by PMA and PHA is involved in various signal transmitters including DR3.) More preferable is DR3 ligand.

The time period for adding the reagent is not limited especially. For example, the reagent may be added for a time period anywhere between 1 to 72 hours, and preferably 12 to 48 hours.

Further, the cells which are not stimulated are used as a control.

(3) The stimulated cells and the control cells are lysed in a solution such as a solubilization buffer, and caspase-8 is detected.

A method of detecting caspase-8 is not limited especially so long as it is a usual method of detecting a protein. For example, it can be conducted by Western blotting.

The Western blotting may be carried out, for example, in the following manner after the protein is electrophoresed on a SDS-polyacrylamide gel, the protein is transferred to a PVDF membrane, and caspase-8 is detected by detection of a labeled anti-caspase-8 antibody binding to the caspase-8.

(4) Results

Regarding healthy subjects, the expression of caspase-8 in the stimulated cells is lower than that of caspase-8 in the unstimulated cells. This is not the case for the RA patients.

The above result indicated that the induction of apoptosis was inhibited due to the abnormal DR3 in RA patients. This is a cause of the RA onset. In other words, it was proper that the mutations of the genome and the transcripts thereof could be used for the diagnosis of RA (the evaluation of the RA onset or the RA onset possibility).

From the above result, concentrations of the measured caspase-8 before and after the stimulation can be compared and, the test subjects who do not show a decrease in concentration can be diagnosed as RA patients or can be determined to have a high RA onset possibility. More specifically, diagnosis of the RA patients or determination of a high RA onset possibility can be given by the detection of other variations that are influenced by the transcripts of the genome.

(c) Use of Normal DR3 in a Therapeutic Method and Remedies for RA

In the joints affected by RA, joint destruction occurs partly by the proliferation of synovial cells. Therefore, anti-Fas antibody that can cause synovial cells to induce apoptosis is considered to be effective as the remedies for RA. Actually, clinical trials of anti-Fas antibody as remedies for RA have been currently advanced. On the other hand, the mutant DR3 caused by the mutations of DR3 genome cannot induce apoptosis, and this is considered to be a cause of the disease in the RA patients having the mutations in DR3. The DR3 belongs to a death receptor family as Fas and can induce apoptosis. Therefore, it is considered that supplement of normal DR3 to the RA patients having the mutations in DR3 causes the induction of apoptosis in the cells, and this is effective as a therapeutic method for RA as is the anti-Fas antibody. Consequently, an object of the present invention is to provide the following therapeutic method and remedies for RA.

A therapeutic method of rheumatoid arthritis, wherein a patient with rheumatoid arthritis, having a mutant DR3 as a transcript of the genome according to the present invention, is supplemented with a normal DR3 not having mutations or DNA coding for the normal DR3, or a low molecular weight compound as an agonist of the normal DR3.

Remedies for rheumatoid arthritis which are used for a therapy of a patient with rheumatoid arthritis, having a mutant DR3 which is a transcript of the genome according to the present invention, the remedies containing, as a primary component, a normal DR3 not having mutations or DNA coding for the normal DR3, or a low molecular weight compound as an agonist of the normal DR3.

Actually, as described later in Example 10, it was recognized from experiment that the supplement of the normal DR3 was useful as a therapeutic method for RA.

A method of supplementing the normal DR3 is not especially limited. For example, a well-known protein expression system or a gene introduction method may be used. More specifically, a method using a vector, such as an expression vector or a virus vector, that is used to cause a mammalian cell to express a protein can be used. Further, in the case where a low molecular weight compound acting as an agonist of a DR3 is supplemented, the low molecular weight compound may specifically be Apo3L, which is well known as a DR3 ligand (Current Biology, Vo. 8, p. 525-528, in 1998), or an anti-DR3 antibody which can act as an agonist. A specific example of the anti-DR3 antibody is the polyclonal antibody described in Immunity (Vol. 6, p. 79-88, in 1997). These compounds may be administered orally or by intravenous injection to the RA patient's body. Note that, the low molecular weight compound herein means a compound, including proteins such as peptides.

Further, the above normal DR3 or the DNA coding for the normal DR3, or the low molecular weight compound as an agonist of the DR3 may be used not only selectively as remedies, but also in combinations. Accordingly, also effective is a therapeutic method using at least one of the above normal DR3 or the DNA coding for the normal DR3, and the low molecular weight compound as an agonist of the DR3

(d) Diagnostic Kit of Rheumatoid Arthritis

The RA diagnostic kit (the evaluation kit of the RA onset or the RA onset possibility) according to the present invention is not especially limited as long as it includes reagents, for example, such as a primer, a probe, and an antibody, capable of detecting the mutations of the genome or of the transcripts, and the kit can also be obtained by a combination with other reagents.

For example, as a kit for detecting the genome named is a kit including a primer designed to amplify a genomic region containing at least one of the above mutations, combined with at least one of the reagents required for the detection of the mutations, such as a probe designed to detect a genomic region containing at least one of the above mutations, a restriction enzyme, regents used by a DNA sequencing method such as the Maxam-Gilbert method and the chain terminator method, and others. Further, preferably named is a kit including a fluorescent-labeled dideoxynucleotide.

For example, as a kit for detecting a protein named is a kit including an antibody that recognizes a mutant protein.

For example, as a kit of detecting mRNA given is a kit including a primer designed to amplify a region containing the mutations, combined with at least one of the reagents required for the detection of the mutations, such as a probe designed to detect a region containing the mutations, a restriction enzyme, regents used by a DNA sequencing method such as the Maxam-Gilbert method and the chain terminator method, and others. Further, preferably given is a kit including a fluorescent-labeled dideoxynucleotide.

By using such a diagnostic (evaluation) kit, it is possible to diagnose RA (to evaluate the RA onset or the RA onset possibility) at high accuracy.

In the diagnostic (evaluation) kit of the present invention, for example, in the case where a primer is included, the primer can be suitably selected in accordance with a detecting method, provided that it can detect at least one of the mutations according to the present invention. Preferably named are a set of a sense primer at positions 2717 to 2736 of SEQ ID NO:1 and an antisense primer at positions 3284 to 3306 of SEQ ID NO:1, a set of a sense primer at positions 1051 to 1078 of SEQ ID NO:1 and an antisense primer at positions 4058 to 4085 of SEQ ID NO:1, and a sense primer at positions 21 to 38 of SEQ ID NO:1 and an antisense primer at positions 1517 to 1535 of SEQ ID NO:1. More preferably named are a set of a sense primer at positions 1534 to 1556 of SEQ ID NO:1 and an antisense primer at positions 3284 to 3306 of SEQ ID NO:1, and a sense primer at positions 667 to 687 of SEQ ID NO:1 and an antisense primer at positions 1517 to 1535 of SEQ ID NO:1. Further, in addition to the primer components, the diagnostic kit may include combinations of one to several reagents in accordance with the detection of the mutations according to the present invention. Note that, the reagents are suitably selected in accordance with the detecting method used. For example, named are restriction enzymes ApaI, dATP, dUTP, dTTP, and dGTP; DNA synthetase; and RNA synthetase. Further, the diagnostic kit may include a proper buffer, a washing solution, or the like, which does not prevent the mutations from being detected.

BEST MODE FOR CARRYING OUT THE INVENTION

Figure 1:
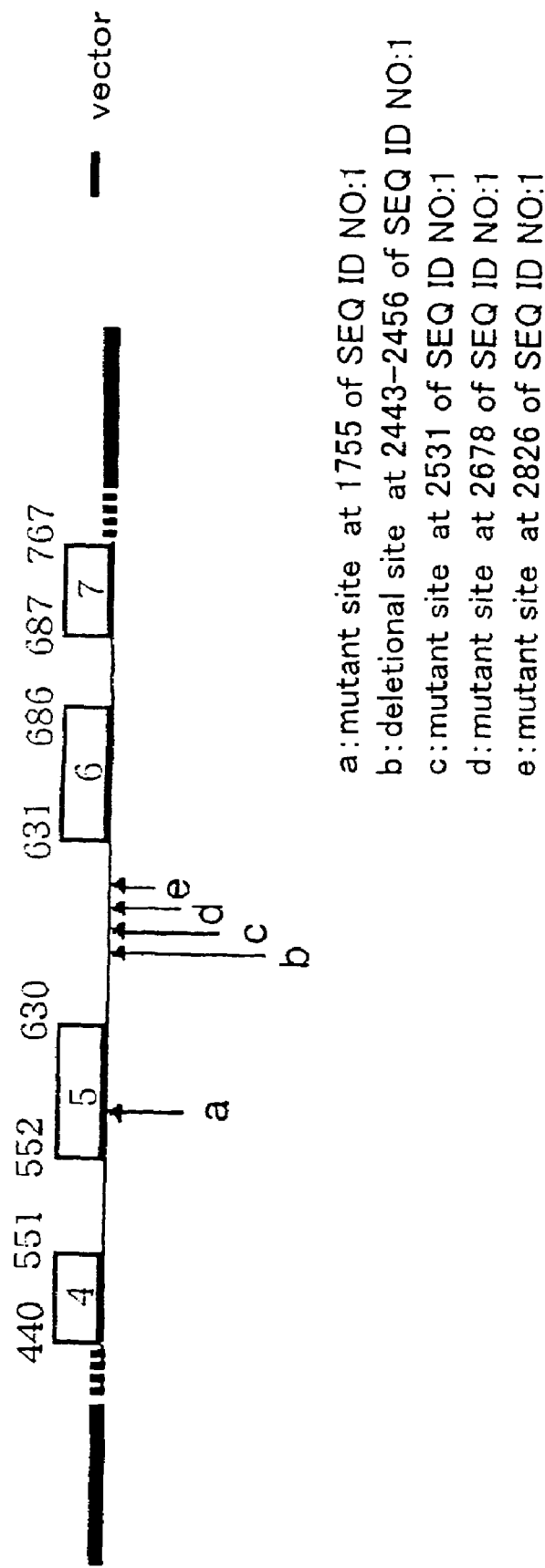
FIG. 1 is a view showing positions of five mutations.

The following will explain the present invention with examples and reference examples. Note that, brevity codes used in the examples and reference examples have the following meanings:

10×Pfu buffer: 200 mM Tris-HCl (pH7.5), 100 mM potassium chloride, 100 mM ammonium sulfate, 20 mM magnesium sulfate, 1% triton X-100, 1 mg/ml bovine serum albumin;

TAE buffer: 0.04M Tris-acetate, 0.002M ethylenediaminetetraacetic acid;

10×L buffer: 100 mM Tris-HCl (pH7.5), 100 mM magnesium chloride, 10 mM dithiothreitol;

10×H buffer: 500 mM Tris-HCl (pH7.5), 100 mM magnesium chloride, 10 mM dithiothreitol, 1000 mM sodium chloride;

10×K buffer: 200 mM Tris-HCl (pH8.5), 100 mM magnesium chloride, 10 mM dithiothreitol, 1000 mM potassium chloride;

10×PCR II buffer: 500 mM potassium chloride, 100 mM Tris-HCl (pH8.3);

10×SSC: 1.5M sodium chloride, 0.15M sodium citrate (pH7.0);

Buffer A: 100 mM Tris-HCl (pH9.5), 300 mM sodium chloride;

FCS: fetal calf serum;

SDS: sodium dodecylsulfate;

BSA: bovine serum albumin;

EDTA: ethylenediaminetetraacetic acid;

IPTG: isopropylthio-β-D-galactoside;

X-gal: 5-bromo-4-chloro-3-indolyl-β-D-galactoside;

PMA: phorbol 12-myristate 13-acetate

PHA: phytohemagglutinin

Solubilization buffer: 50 mM Tris-HCl (pH7.5), 150 mM sodium chloride, 1% NP40, 0.5% sodium deoxycholate, protease inhibitor cocktail;

2× sample buffer: 50 mM Tris-HCl (pH6.8), 10% glycerol, 2% SDS, 2% β-mercaptoethanol, 0.1% bromophenol blue;

TBS solution: 20 mM Tris-HCl (pH7.6), 137 mM sodium chloride;

Tween 20: polyoxyethylene (20) sorbitan monolaurate;

TBS-T solution: 20 mM Tris-HCl (pH7.6), 137 mM sodium chloride, 0.05% Tween 20;

HRP: horseraddish peroxidase;

Washing buffer: 50 mM Tris-HCl (pH7.5), 1M sodium chloride, 0.1% NP40, 0.05% sodium deoxycholate, protease inhibitor cocktail Note that, "M" and "mM" represent "mol/L" and "mmol/L", respectively; and "solution" herein means aqueous solution unless otherwise stated.

EXAMPLE 1

Detection of a Base Sequence Having Mutations in DR3 Genome (1) Genomic DNA was prepared from peripheral blood of a healthy subject and an RA patient by guanidine thiocyanate method (Japan Society of Blood Transfusion Magazine, Vol. 40, No. 2, p. 413, in 1994). More specifically, to 10 ml of peripheral blood drawn using EDTA was added 20 ml of cell membrane lysis solution (solution I: 0.32M sucrose, 1% (v/v) Triton X-100, 5 mM magnesium chloride, 12 mM Tris-HCl (pH7.6)). After mixed by inversion, the mixture solution was centrifuged at 3000 rpm for 10 minutes to collect nuclei. To the collected nuclei was added 5 ml of nuclear membrane lysis solution (solution II: 4M guanidine thiocyanate, 12 mM EDTA, 375 mM sodium chloride, 0.5% sodium N-dodecanoyl sarcosyl, 0.1 M β-mercaptoethanol, 12 mM Tris-HCl (pH7.6)). The mixture solution was heated at 55° C. for 10 minutes, and the genomic DNA was prepared by ethanol precipitation.

(2) To 50 ng genomic DNA obtained was added 2.5 μl of 10×LA buffer (product name: manufactured by Takara Shuzo Co., Ltd.), 2.5 μl of 25 mM magnesium chloride, 4 μl of 2.5 mM deoxynucleotide mixture solution, 0.25 µl of 20 µM sense primer, 0.25 µl of 20 µM antisense primer, and 1.25U DNA polymerase reagent (LA Taq DNA polymerase: manufactured by Takara Shuzo Co., Ltd.). The mixture solution had a total volume of 25 µl after addition of sterile distilled water, and a PCR reaction was carried out. The PCR reaction was performed under the following conditions: 35 cycles of denaturation at 98° C. for 20 seconds, and simultaneous annealing and extension reaction at 68° C. for 5 minutes. The obtained PCR products were purified by the commercially-available kit (QIAquick PCR Purification Kit: manufactured by Qiagen, Inc.). The sense primer and antisense primer used were oligonucleotides corresponding to the base sequence at positions 1051 to 1078 and the base sequence at positions 4058 to 4085 of SEQ ID NO:1, respectively.

(3) The sequence reaction of the purified PCR products was performed using a commercially-available kit (BigDye Terminator Cycle Sequencing Ready Reaction Kit: manufactured by Perkin-Elmer Co.) by dye terminator method.

To 50 ng of the PCR products were added 4 µl of mixture reagent (Terminator Ready Reaction Mix: manufactured by Perkin-Elmer Co.) and 1.6 pmol of primers, and a total volume of the mixture solution was 101 µl after addition of sterile distilled water. The sequence reaction was performed with 25 cycles under the following conditions: at 96° C. for 10 seconds, at 50° C. for 5 seconds, and at 60° C. for 4 minutes. 1 µl of 3M sodium acetate (adjusted to pH5.2 with acetic acid) and 25 µl of 95% ethanol were added to the reaction solution and cooled on ice for 15 minutes. After the reaction solution was centrifuged at 15000 rpm for 20 minutes, precipitation was washed with 125 µl of 70% ethanol and dried. The obtained precipitation was solubilized in formaldehyde-blue dextran (5:1) solution and heat-treated at 95° C. for 2 minutes, and the base sequence was determined using a sequencer (ABI PRISM377 DNA Sequencer: manufactured by Perkin-Elmer Co.).

The used primers were oligonucleotides corresponding to the base sequence at positions 1535 to 1552 of SEQ ID NO:1 and oligonucleotides corresponding to the complementary strand at positions 2892 to 2912 of SEQ ID NO:1.

As a result of this, from the DR3 genome of RA patients found were single base polymorphism and a deletion of bases, as indicated in the following (1) through (5) in the genomes of the healthy subjects in the SEQ ID NO:1.

(1) A adenine (A) to guanine (G) substitution of the base at position 1755

(2) A deletion of the bases at positions 2443 to 2456

(3) A cytosine (C) to thymine (T) substitution of the base at position 2531

(4) A adenine (A) to thymine (T) substitution of the base at position 2678

(5) A adenine (A) to guanine (G) substitution of the base at position 2826

EXAMPLE 2

Detection of Deletion at Positions 2443 to 2456 in the Base Sequence of SEQ ID NO:1

(1) To 50 ng genomic DNA was added 2.5 µl of 10×LA buffer (product name: manufactured by Takara Shuzo Co., Ltd.), 2.5 µl of 25 mM magnesium chloride, 4 µl of 2.5 mM deoxynucleotide mixture solution, 0.25 µl of 20 µM sense primer, 0.25 µl of 20 µM antisense primer, and 1.25U DNA polymerase reagent (LA Taq DNA polymerase: manufactured by Takara Shuzo Co., Ltd.). The mixture solution had a total volume of 25 µl after addition of sterile distilled water, and a PCR reaction was carried out. The PCR reaction was performed under the following conditions: 35 cycles of thermal denaturation at 95° C. for 1 minute, annealing at 63° C. for 1 minute, and extension reaction at 72° C. for 1 minute. The sense primer and antisense primer used were oligonucleotides corresponding to the base sequence at positions 1534 to 1556 and the base sequence at positions 3284 to 3306 of SEQ ID NO:1, respectively. Together with molecular weight marker (100 bp ladder: manufactured by New England Biolabs (NEB) Co.) the resultant was electrophoresed on agarose gel (1% Agarose S: manufactured by Nippon Gene Co., Ltd.) in TAE buffer. Approximately 1.5 kbp of the PCR products was collected from the gel and purified by a commercially-available kit (QIA quick Gel Extraction Kit: manufactured by Qiagen, Inc.). 50 ng of the PCR products obtained, 25 ng of TA cloning vector (pT7BlueT vector: manufactured by Novagen Co.), and 3 µl of T4DNA ligase solution (solution I of DNA ligation kit Ver II: manufactured by Takara Shuzo Co., Ltd.) were mixed, and the mixture was subjected to ligation at 16° C. for 2 hours.

(2) The total volume of the obtained ligation solution was mixed with competent cell DH5α and incubated on ice for 30 minutes. Next, after heat-shocked in a water bath at 42° C. for 20 seconds, the mixture solution was cooled on ice for 2 minutes. 900 µl of SOC culture medium was added to the mixture solution and shake-cultured at 37° C. for 1 hour. This culture solution was inoculated onto LB plate including X-gal 0.1 mM, IPTG 0.1 mM, and 50 µg/ml of ampicillin and cultured at 37° C. overnight, which brought the formation of colonies.

(3) A single colony was picked and transferred onto 1.5 ml of LB culture medium including 50 µg/ml of ampicillin, and cultured at 37° C. overnight. The culture solution was centrifuged, and a precipitate whose supernatant was removed was suspended in 100 µl of the solution 1 (50 mM glucose, 10 mM EDTA, and 25 mM Tris-HCl (pH 8.0)). To the resultant solution was added 200 µl of alkaline solution (0.2M sodium hydrate, 1% SDS). After mixed gently, the mixture solution was incubated on ice for 5 minutes. Further, 150 µl of 3M potassium acetate solution (adjusted to pH5.5 with acetic acid) was added to the mixture solution, and it was incubated on ice for 5 minutes. After the obtained solution was centrifuged at 12000 rpm for 5 minutes, 400 µl of phenol chloroform (1:1) solution was added to its supernatant and centrifuged at 12000 rpm for 5 minutes. After 800 µl of ethanol was added to aqueous layer, followed by centrifugation at 12000 rpm for 5 minutes, the supernatant was removed. After the precipitation was washed with 70% ethanol, it was dried and solubilized in 50 µl of sterile distilled water. After 0.5 µl of 1 mg/ml RNase A (manufactured by Sigma Chemical Company) was added to the obtained solution, followed by incubation at 37° C. for 1 hour, 30 µl of 20% polyethyleneglycol/2.5M sodium chloride solution was added to the resultant solution and allowed to stand on ice for 1 hour. The obtained solution was centrifuged at 12000 rpm for 10 minutes, and its precipitation was washed with 70% ethanol, dried, and solubilized in 30 µl of sterile distilled water.

(4) The sequence reaction of plasmid DNA was performed using a commercially-available kit (BigDye Terminator Cycle Sequencing Ready Reaction Kit: manufactured by Perkin-Elmer Co.) by dye terminator method.

To 300 ng of plasmid DNA was added 4 µl of mixture reagent (Terminator Ready Reaction Mix: manufactured by Perkin-Elmer Co.) and 1.6 pmol of primers, and a total volume of the mixture solution was 10 µl after addition of sterile distilled water. The sequence reaction was performed with 25 cycles under the following conditions: at 96° C. for 10 seconds, at 50° C. for 5 seconds, and at 60° C. for 4 minutes. 1 µl of 3M sodium acetate (adjusted to pH5.2 with acetic acid) and 25 µl of 95% ethanol were added to the reaction solution and cooled on ice for 15 minutes. After the obtained solution was centrifuged at 15000 rpm for 20 minutes, its precipitation was washed with 125 µl of 70% ethanol and dried. The obtained precipitation was solubilized in formaldehyde/blue dextran (5:1) solution and heat-treated at 95° C. for 2 minutes, and the base sequence was determined using a sequencer (ABI PRISM377 DNA Sequencer: manufactured by Perkin-Elmer Co.). The used primers were oligonucleotides corresponding to the base sequence of the complementary strand at positions 2892 to 2912 of SEQ ID NO:1.

As a result, it was found that the clone that was obtained by subcloning the PCR products resulting from the amplification of the genomes having the mutations had a deletion of the base sequence at positions 2443 to 2456 of SEQ ID NO:1.

EXAMPLE 3

Electrophoretic Detection of Deletion at Positions 2443 to 2456 in the Base Sequence of SEQ ID NO:1

Figure 2:
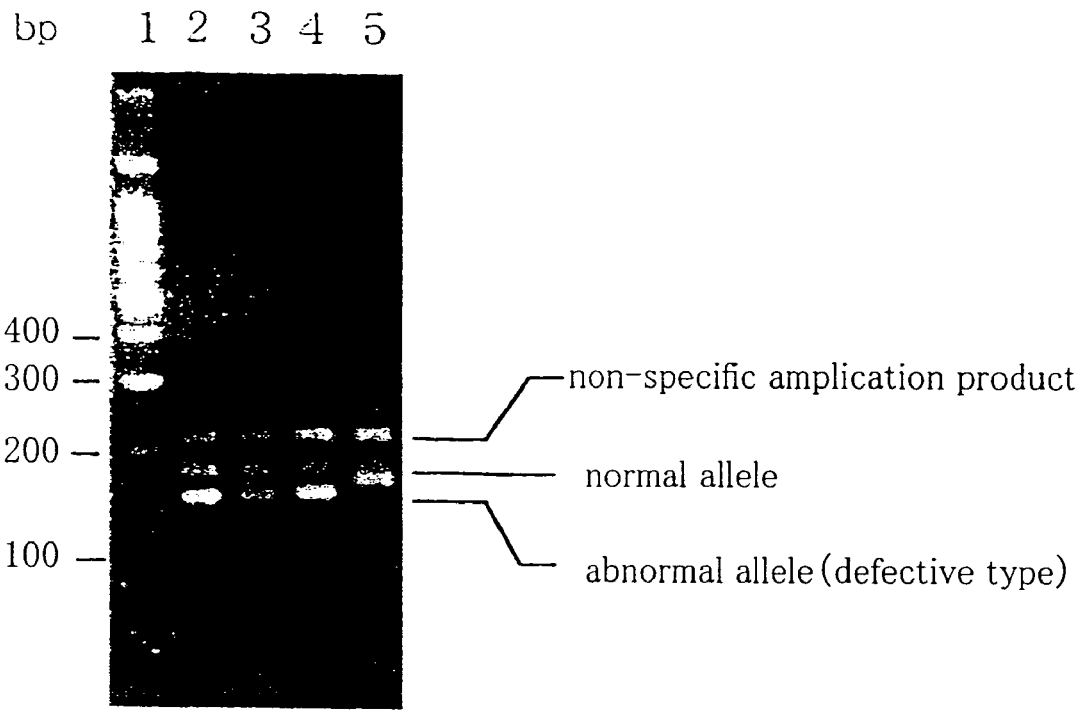
FIG. 2 is an electrophoretogram showing the electrophoretic patterns of normal and defective alleles.

To 50 ng of genomic DNA was added 2.5 µl of 10×Pfu buffer (manufactured by Stratagene Co.), 2 µl of 2.5 mM deoxynucleotide mixture solution, 0.25 µl of 20M sense primer, 0.25 µl of 20 µM antisense primer, and 1.25U DNA polymerase reagent (Pfu DNA polymerase: manufactured by Stratagene Co.). The mixture solution had a total volume of 25 µl after addition of sterile distilled water, and a PCR reaction was carried out. The PCR reaction was performed under the following conditions: after initial denaturation at 95° C. for 1 minute, 40 cycles of thermal denaturation at 95° C. for 1 minute, annealing at 55° C. for 1 minute, and extension reaction at 72° C. for 1 minute. The used primers, sense primer and antisense primer, were oligonucleotides corresponding to the base sequence at positions 2369 to 2389 and the base sequence at positions 2514 to 2535 of SEQ ID NO:1, respectively. The amplified PCR products with molecular weight marker (100 bp ladder: manufactured by New England Biolabs (NEB) Co.) was electrophoresed on agarose gel (3% GTG Agarose: manufactured by Takara Shuzo Co., Ltd.) in TAE buffer and visualized in an ethidium bromide solution. The result is shown in FIG. 2.

In the specimen having a normal allele and a defective allele were detected two amplified products which were different in their molecular weights. In the specimen having only normal alleles detected was only an amplified product having a large molecular weight.

EXAMPLE 4

Detection of Aberrant Splicing Caused by Five Mutations of SEQ ID NO:1

(1) To 50 ng of the genomic DNA of healthy subjects or RA patients were added 2.5 µl of 10×LA buffer (product name: manufactured by Takara Shuzo Co., Ltd.), 2.5 µl of 25 mM magnesium chloride, 4 µl of 2.5 mM deoxynucleotide mixture solution, 0.25 µl of 20M sense primer, 0.25 µl of 20 µM antisense primer, and 1.25U of DNA polymerase reagent (LA Taq DNA polymerase: manufactured by Takara Shuzo Co., Ltd.). The mixture solution had a total volume of 25 µl after addition of sterile distilled water, and a PCR reaction was carried out. The PCR reaction was performed under the following conditions: after initial denaturation at 95° C. for 1 minute, 35 cycles of thermal denaturation at 95° C. for 1 minute, annealing at 63° C. for 1 minute, and extension reaction at 72° C. for 2 minute. The primers used for the reaction are shown below.

```
Sense primer A:                         (SEQ ID NO:6)
5'-GGGGTAGCATCCGCTTCCTGCCCCAGCCAGGCTGGTTTGTGGAG-
TGG-3'

Antisense primer A:                     (SEQ ID NO:7)
5'-CCGCTCGAGGGGCCACCTCCAGTGCCAGTGGCGGTATGTGTAG-
GTCAGG-3'
```

The amplified PCR products were purified by ethanol precipitation. To obtained PCR products were added 10 units of Kpn I (manufactured by Takara Shuzo Co., Ltd.), 3 µl of 10×L buffer (manufactured by Takara Shuzo Co., Ltd.). The mixture solution had a total volume of 30 µl after addition of sterile distilled water. The reaction solution was incubated at 37° C. for 4 hours, followed by addition of 10 units of Xho I (manufactured by Takara Shuzo Co., Ltd.) and 4 µl of 10×H buffer (manufactured by Takara Shuzo Co., Ltd.). The mixture solution had a total volume of 40 µl after addition of sterile distilled water and further incubated at 37° C. for 4 hours. The reaction solution with molecular weight marker (1 kbp ladder: manufactured by Fermentas Inc.) was electrophoresed on agarose gel (1% Agarose S: manufactured by Nippon Gene Co., Ltd.) in TAE buffer. Approximately 1.8 kbp of the PCR products obtained was collected from the gel and purified by the commercially-available kit (QIAquick Gel Extraction Kit: manufactured by Qiagen, Inc.).

(2) To 3 µg of pcDNA3.1 vector (product name: manufactured by Invitrogen Corp.), 10 units of Kpn I (manufactured by Takara Shuzo Co., Ltd.), 3 µl of 10×L buffer (manufactured by Takara Shuzo Co., Ltd.). The mixture solution had a total volume of 30 µl after addition of sterile distilled water. The reaction solution was incubated at 37° C. for 4 hours, followed by addition of 10 units of Xho I (manufactured by Takara Shuzo Co., Ltd.) and 4 µl of 10×H buffer (manufactured by Takara Shuzo Co., Ltd.). The mixture solution had a total volume of 40 µl after addition of sterile distilled water and further incubated at 37° C. for 4 hours. The reaction solution with a molecular weight marker (1 kbp ladder: manufactured by Fermentas Inc.) was electrophoresed on agarose gel (1% Agarose S: manufactured by Nippon Gene Co., Ltd.) in TAE buffer. Approximately 5.6 kbp of DNA band was collected from the gel and purified by the commercially-available kit (QIAquick Gel Extraction Kit: manufactured by Qiagen, Inc.).

(3) 50 ng of the PCR products purified in Example 4 (1) and 35 ng of pcDNA3.1 vector purified in Example 4 (2) were mixed with 4 µl of T4DNA ligase solution (solution I of DNA ligation kit Ver II: manufactured by Takara Shuzo Co., Ltd.), and the mixture was subjected to ligation at 16° C. for 4 hours.

(4) The resultant solution was subjected to transformation as by the methods in Example 2 (2) and (3), which brought the preparation of plasmid DNA.

(5) The sequence reaction of plasmid DNA was performed using the commercially-available kit (BigDye Terminator Cycle Sequencing Ready Reaction Kit: manufactured by Perkin-Elmer Co.) by dye terminator method.

To 300 ng of plasmid DNA were added 4 μl of mixture reagent (Terminator Ready Reaction Mix: manufactured by Perkin-Elmer Co.) and 1.6 pmol of primers, and a total volume of the mixture solution was 10 μl after addition of sterile distilled water. The sequence reaction was performed with 25 cycles under the following conditions: at 96° C. for 10 seconds, at 50° C. for 5 seconds, and at 60° C. for 4 minutes. 1 μl of 3M sodium acetate (adjusted to pH5.2 with acetic acid) and 25 μl of 95% ethanol were added to the reaction solution and cooled on ice for 15 minutes. After the obtained solution was centrifuged at 15000 rpm for 20 minutes, its precipitation was washed with 125 μl of 70% ethanol and dried. The obtained precipitation was solubilized in 3 μl of formaldehyde/blue dextran (5:1) solution and heat-treated at 95° C. for 2 minutes. Next, the base sequence was determined using a sequencer (ABI PRISM377 DNA Sequencer: manufactured by Perkin-Elmer Co.), and constructed were a normal vector having no mutation and a mutant vector having A to G substitution of the base at position 1755 of SEQ ID NO:1, deletion of the bases at positions 2443 to 2456 of SEQ ID NO:1, C to T substitution of the base at position 2531 of SEQ ID NO:1, A to T substitution of the base at position 2678 of SEQ ID NO:1, and A to G substitution of the base at position 2826 of SEQ ID NO:1 (see FIG. 1).

(6) 10 μg of the constructed normal vector or mutant vector and 1×10$^6$ of Jurkat cells suspended in 0.25 ml of RPMI1640/20% FCS were put into a cuvette of 0.4 mm gap (manufactured by BM Equipment Co., Ltd.) and allowed to stand still at room temperature for 10 minutes. Using an electroporater (Gene pulser II: manufactured by Bio-rad Laboratories, Inc.), the mixture was subjected to transfection under the conditions of 200V and 950 μF. After electroshock, the mixture was allowed to stand on ice for 10 minutes. The total volume of the mixture was 4 ml by adding RPMI1640/10% FCS and cultured at 37° C. on 6 well plate in 5% CO$_2$ for 24 hours. The cells to which 20 ng/ml of PMA (manufactured by Sigma Chemical Company) and 1 μg/ml of PHA (manufactured by Difco Laboratories) were further cultured for 24 hours.

After the collected cells were washed in phosphate buffered saline, total RNA was prepared using Trizol reagent (product name: manufactured by Gibco-BRL) by guanidine thiocyanate phenol chloroform (AGPC) method. 1 μg of the obtained total RNA after further process with DNase (manufactured by Nippon Gene Co., Ltd.) was subjected to usual reverse transcription using a reverse transcription reaction kit (RNA PCRKit: manufactured by Perkin-Elmer Co.), and cDNA was prepared.

To 5 μl of cDNA solution obtained were added 2 μl of 10×PCR II buffer (manufactured by Perkin-Elmer Co.), 1 μl of 25 mM magnesium chloride, 0.25 μl of 20 μM sense primer, 0.25 μl of 20 μM antisense primer, and 1.25U DNA polymerase reagent (Ampli Taq Cold DNA polymerase: manufactured by Perkin-Elmer Co.). The mixture solution had a total volume of 25 μl after addition of sterile distilled water and subjected to PCR reaction. The PCR reaction was performed under the following conditions: after initial denaturation at 95° C. for 10 minutes, 40 cycles of thermal denaturation at 95° C. for 1 minute, annealing at 55° C. for 1 minute, extension reaction at 72° C. for 1 minute, and final extension reaction at 72° C. for 5 minutes. The primers used for the reaction are shown below.

```
Sense primer B:
5'-ATCCGCTTCCTGCCCC-3'         (SEQ ID NO:8)

Antisense primer B:
5'-GGGGCCACCTCCAGTGCC-3'       (SEQ ID NO:9)
```

Note that, the base sequences of the primers B are oligonucleotide corresponding to partial base sequences of the sense primer A and the antisense primer A, respectively.

(7) The obtained RT-PCR solution with a molecular weight marker (1 kbp ladder: manufactured by Fermentas Inc.) was electrophoresed on agarose gel (2% Agarose S: manufactured by Nippon Gene Co., Ltd.) in TAE buffer and visualized in an ethidium bromide solution. The PCR products were collected from the gel and purified by the commercially-available kit (QIAquick Gel Extraction Kit: manufactured by Qiagen, Inc.). 50 ng of the obtained PCR products and 25 ng of TA cloning vector (pT7BlueT vector: manufactured by Novagen, Co.) were mixed with 3 μl of T4DNA ligase solution (solution I of DNA ligation kit Ver II: manufactured by Takara Shuzo Co., Ltd.), and the mixture solution was subjected to ligation at 16° C. for 2 hours.

(8) By the same method as the method described in Example 2, plasmid DNA was prepared, and the base sequence was determined. The used primers were oligonucleotides shown in the sense primer B and the antisense primer B.

As a result, in the vector into which an A to G mutation at position 1755 in the base sequence of SEQ ID NO:1, a deletion at positions 2443 to 2456 in the base sequence of SEQ ID NO:1, a C to T mutation at position 2531 in the base sequence of SEQ ID NO:1, an A to T mutation at position 2678 in the base sequence of SEQ ID NO:1, and an A to G mutation at position 2826 in the base sequence of SEQ ID NO:1, mRNA holding positions 2636 to 2792 of SEQ ID NO:1 were detected.

EXAMPLE 5

Detection of Aberrant Splicing by Southern Blotting (1) The obtained RT-PCR solution with molecular weight marker (1 kbp ladder: manufactured by Fermentas Inc.) was electrophoresed on agarose gel (2% Agarose S: manufactured by Nippon Gene Co., Ltd.) in TAE buffer. The gel was immersed into a denaturation solution (0.5M sodium hydroxide, 1.5M sodium chloride) for 25 minutes, and further immersed into a neutralization solution (0.5M Tris-HCl (pH7.5), 1.5M sodium chloride) for 30 minutes. By capillary method, DNA inside the gel was transferred to a nylon membrane (Hybond-N+: manufactured by Amersham Pharmacia Biotech Ltd.) overnight, and the DNA was immobilized on the membranes using UV crosslinker (manufactured by NIPPON Genetics Co., Ltd.). The buffer used for the capillary was 10×SSC. Hybridization and detection of the DNA fragments were performed as follows, using the Gene Images 3'-oligolabeling·CDP-Star detection system (manufactured by Amersham Pharmacia Biotech Ltd.). The membranes on which the DNA was immobilized was immersed into a hybridization buffer (5×SSC, 0.1% (w/v) SDS, 0.5% (w/v) dextran sulfate of molecular weight 500000 (manufactured by Sigma Chemical Company), and 5% (v/v) blocking reagent attached to the kit), and was subjected to pre-hybridization while being shaken at 59° C. for 30 minutes.

Figure 3:
FIG. 3 is an X-ray photograph detecting abnormal splicing due to five mutations by Southern blotting.

(2) By using a commercially-available kit (Gene Images 3'-oligolabeling kit), an oligonucleotide having the base sequence at positions 2715 to 2736 of SEQ ID NO:1 were fluorescein-labeled to use it as a probe. The probe was added to a pre-hybridization solution to 10 ng/ml and further subjected to hybridization at 59° C. for 2 hours while being shaken. After washed in the buffer (5×SSC, 0.1% (w/v) SDS) twice for 5 minutes each time, the resultants were washed twice for 15 minutes each in a buffer (1×SSC, 0.1% (w/v) SDS) that had been previously heated to 50° C. The membranes were quickly rinsed in the Buffer A and subjected to blocking at room temperature for 1 hour using a blocking reagent, which is part of the kit, diluted 10 times with the buffer A. The membranes were quickly rinsed in the buffer A, immersed into antibody-diluted solution (the solution of alkaline phosphatase-labeled anti-fluorescein antibody, which is part of the kit, diluted 5000 times with the buffer A including 0.5% (w/v) BSA), and incubated at room temperature for 1 hour. The membranes were washed three times each for 10 minutes in the buffer A containing 0.3% (v/v) Tween20 while being shaken at room temperature. The membranes were quickly rinsed in the buffer A and immersed into a detection reagent attached to the kit, followed by exposure to X-ray film (manufactured by Fuji Photo Film Co., Ltd.). The result is shown in FIG. 3.

Transcripts binding to the probe only in the mutant vector was detected, and aberrant splicing caused by five mutations was detected.

EXAMPLE 6

Detection of Aberrant Splicing Caused by the Mutation of the Position 2678 of SEQ ID NO:1

(1) The normal vector prepared in Example 4(5) was caused to have an A to G mutation at position 1755 in the base sequence of SEQ ID NO:1, a C to T mutation at position 2531 in the base sequence of SEQ ID NO:1, an A to T mutation at position 2678 in the base sequence of SEQ ID NO:1, and an A to G mutation at position 2826 in the base sequence of SEQ ID NO:1, using a commercially-available kit (QuickChange™Site-Directed Mutagenesis kit: manufactured by Stratagene Co.) by the following method.

(2) To 50 ng of normal vector were added 1 μl of 2.5 mM deoxynucleotide mixture solution, 2.5 μl of 10×Pfu buffer, 2.5U of DNA polymerase reagent (Pfu Turbo DNA polymerase: manufactured by Stratagene Co.), 62.5 ng of sense primer, and 62.5 ng of antisense primer. The mixture solution had a total volume of 25 μl after addition of sterile distilled water. The PCR reaction was performed under the following conditions: after initial denaturation at 95° C. for 30 seconds, 12 cycles of thermal denaturation at 95° C. for 30 seconds, annealing at 55° C. for 1 minute, and extension reaction at 68° C. for 15 minutes. The amplified products were digested with Dpn I. 1 μl of the reaction solution was mixed with competent cell XL-1 Blue, and incubated on ice for 30 minutes. After immersed into a water bath at 42° C. for 30 seconds for addition of heat-shock, the reaction solution was cooled on ice for 2 minutes. NZY culture medium was added to the reaction solution and shake-cultured at 37° C. for 1 hour. This culture solution was inoculated on LB plate including 50 μg/ml of ampicillin and cultured at 37° C. overnight, which brought the formation of colonies. By the same method as that described in Example 2(3) and (4), plasmid DNA was prepared, the base sequence was determined, and mutant vectors were made in which mutations were introduced at the respective positions. The primers used for the reaction are shown as follows.

The introduction of an A to G mutation at the position 1755 in the base sequence of SEQ ID NO:1

```
Sense primer:
5'-GGTTCCCGCAGAGGTACTGACTGTGGGA-3'    (SEQ ID NO:10)

Antisense primer:
5'-TCCCACAGTCAGTACCTCTGCGGGAACC-3'    (SEQ ID NO:11)
```

The introduction of a C to T mutation at the position 2531 in the base sequence of SEQ ID NO:1

```
Sense primer:
5'-CTTGGCTCACTATAACCTCTGCTGCCTGGG-3'  (SEQ ID NO:12)

Antisense primer:
5'-CCCAGGCAGCAGAGGTTATAGTGAGCCAAG-3'  (SEQ ID NO:13)
```

The introduction of an A to T mutation at the position 2678 in the base sequence of SEQ ID NO:1

```
Sense primer:
5'-GATGGTCTTGATCTCCTGACCTCGTGATCC-3'  (SEQ ID NO:14)

Antisense primer:
5'-GGATCACGAGGTCAGGAGATCAAGACCATC-3'  (SEQ ID NO:15)
```

The introduction of an A to G mutation at the position 2826 in the base sequence of SEQ ID NO:1

```
Sense primer:
                                     (SEQ ID NO:16)
5'-GCAACAGGGGACAGAATAGGCAAAATCCCTG-3'

Antisense primer:
                                     (SEQ ID NO:17)
5'-CAGGGATTTTGCCTATTCTGTCCCCTGTTGC-3'
```

Figure 4:
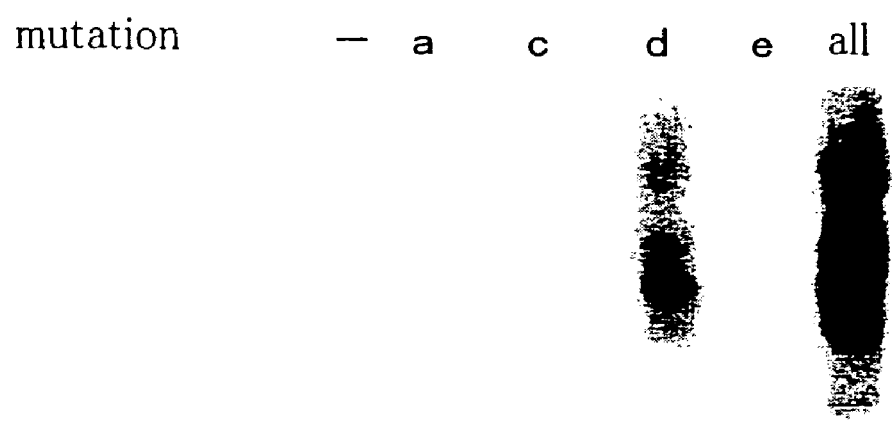
FIG. 4 is an X-ray photograph detecting abnormal splicing caused by the mutation at position 2678 of SEQ ID NO:1 by Southern blotting.

(3) The mutant vector made by the same method as that in Example 4(6) were subjected to transfection to Jurkat cells and subjected to RT-PCR under the same condition of Example 4(6). Furthermore, the resultant was subjected to Southern blotting by the same method as that described in Example 5. The result is shown in FIG. 4.

Only in the vector into which the A to T mutation was introduced at the position 2678 of SEQ ID NO:1, a band showing the binding to the probe was detected, and this mutation was proved to cause aberrant splicing.

EXAMPLE 7

Detection of Mutations in RA Patients

By the same method as that in Example 1 (1) to (3), the mutation in the genomes of RA patients was examined.

As a result, the mutations were observed in 6 out of 60 cases in the group of RA patients having a relative with RA other than themselves (hereinafter referred to as RA families), 4 out of 31 cases in healthy members in RA families, 11 out of 494 cases in the group of RA patients having no relatives with RA other than themselves, and 3 out of 481 cases in generally healthy persons. The mutations in RA families were found at a significantly high rate. Note that, many of the observed mutations were heterozygous.

EXAMPLE 8

Detection of the Base Sequence Having Mutation in DR3 Genome (1) Genomic DNA was prepared from the peripheral blood by the guanidine thiocyanate method (Japan Society of Blood Transfusion Magazine, Vol. 40, No. 2, p. 413, in 1994). More specifically, to 10 ml of peripheral blood drawn using EDTA was added 20 ml of cell membrane lysis solution (solution I: 0.32M sucrose, 1% (v/v) Triton X-100, 5 mM magnesium chloride, 12 mM Tris-HCl (pH7.6)). After mixed by inversion, the mixture solution was centrifuged at 3000 rpm for 10 minutes to collect nuclei. To the collected nuclei was added 5 ml of nuclear membrane lysis solution (solution II: 4M guanidine thiocyanate, 12 mM EDTA, 375 mM sodium chloride, 0.5% sodium N-dodecanoyl sarcosyl, 0.1M β-mercaptoethanol, 12 mM Tris-HCl (pH7.6)). The mixture solution was heated at 55° C. for 10 minutes, and the genomic DNA was prepared by ethanol precipitation.

(2) To 50 ng genomic DNA obtained was added 2.5 µl of 10×PCR buffer (product name: manufactured by Perkin-Elmer Co.), 2.5 µl of 25 mM magnesium chloride, 5 µl of 2 mM deoxynucleotide mixture, 0.25 µl of 20 µM sense primer, 0.25 µl of 20 µM antisense primer, and 1.25U DNA polymerase reagent (AmpliTaq GOLD: manufactured by Perkin-Elmer Co.). The mixture solution had a total volume of 25 µl after addition of sterile distilled water, and a PCR reaction was carried out. The PCR reaction was performed under the following conditions: after enzymatic activation reaction at 95° C. for 10 minutes, 40 cycles of thermal denaturation at 95° C. for 1 minute, and annealing at 60° C. for 1 minute, extension reaction at 72° C. for 2 minutes, and final extension reaction at 72° C. for 5 minutes. The obtained PCR products were purified using multi-screen PCR (product name: manufactured by Millipore, Co.) by automated-dispensing robot (Biomek 2000: manufactured by Beckman Coulter, Inc.). The sense primer and antisense primer used were oligonucleotides corresponding to the base sequence at positions 21 to 38 and the base sequence at positions 1517 to 1535 of SEQ ID NO:1, respectively.

(3) The sequence reaction of the purified PCR products was performed using the commercially-available kit (Big-Dye Terminator Cycle Sequencing Ready Reaction Kit: manufactured by Perkin-Elmer Co.) by dye terminator method.

To 50 ng of the PCR products was added 4 µl of mixture reagent (Terminator Ready Reaction Mix: manufactured by Perkin-Elmer Co.) and 1.6 pmol of primers, and a total volume of the mixture solution was 10 µl after addition of sterile distilled water. The sequence reaction was performed with 25 cycles under the following conditions: at 96° C. for 10 seconds, at 50° C. for 5 seconds, and at 60° C. for 4 minutes. Non-reactive deoxynucleotides from the samples after the sequence reaction were removed by the gel filtration method using sephadex G-50 (manufactured by Amersham Pharmacia Biotech Ltd.) and multi-screen-HV (product name: Millipore, Co.). To the purified sequence products was added 10 µl of sterile distilled water, the mixture solution was heat-treated at 96° C. for 2 minutes, and the base sequence was determined using a sequencer (ABI PRISM3700 DNA Analyzer: manufactured by Perkin-Elmer Co.).

The used sequence primer was oligonucleotide corresponding to the base sequence of the complementary strand at positions 1073 to 1102 of SEQ ID NO:1.

As a result, in DR3 genomes of the RA patients was found the C to T single nucleotide polymorphism at the position 921 of SEQ ID NO:1.

The base at position 921 corresponds to the base at position −53 when the base at the 5'-end of Exon 3 in the sequence registered as cDNA in the GenBank (accession number NM-003790) is used as a reference and the adjacent base of the preceding intron is position −1.

EXAMPLE 9

Detection of Mutations in RA Patients

By the same method as that in Example 8 (1) to (3), the mutation in the genomes of RA patients was examined.

As a result, the mutations were found in 6 out of 43 cases in RA patients of RA families, 4 out of 25 cases in healthy members of RA families. In the 10 individuals who carried the mutations were simultaneously found single base mutations at the positions 1755, 2531, 2678, and 2826 and the base deletion at positions 2443 to 2456 of SEQ ID NO:1. In other words, the above six-base mutations and deletion occurred simultaneously. Note that, many of the observed mutations were heterozygous.

REFERENCE EXAMPLE 1

Experiment on Binding Normal and Mutant DR3 Proteins (1) Preparation of DR3 cDNA 10 ml of peripheral blood drawn using heparin from RA patients was mixed with the equivalent volume of phosphate buffer (PBS), and the reaction mixture was overlaid upon 20 ml of Lymphoprep (Daiichi Pure Chemicals Co., Ltd.). After centrifugation at 1500 rpm for 30 minutes, the layer of peripheral-blood mononuclear cells were collected and washed in PBS. The cells were suspended on culture medium (RPM11640/10% FCS) so as to be $5 \times 10^5$ cells/ml. 10 ml of the cell suspension was sprayed over a 10 cm plate and cultured at 37° C. in 5% of $CO_2$ for 48 hours, with stimulation of 20 ng/ml of PMA (Sigma Chemical Company) and 1 µg/ml of PHA (Difco Laboratories). 1 ml of Trizol reagent (product name: Gibco-BRL) is added to the obtained cells, and total RNA was prepared by thiocyanic acid guanidine phenol chloroform (AGPC) method. From the total RNA, cDNA was prepared using reverse transcription reaction kit (RNA PCR Kit: manufactured by Perkin-Elmer Co.) by usual reverse transcription reaction.

(2) To 5 µl of the cDNA solution obtained were added 2 µl of 10×PCR II buffer (manufactured by Perkin-Elmer Co.), 1 µl of 25 mM magnesium chloride, 0.25 µl of 20 µM sense primer, 0.25 µl of 20 µM antisense primer, and 1.25U DNA polymerase reagent (Ampli Taq Cold DNA polymerase: manufactured by Perkin-Elmer Co.). The mixture solution had a total volume of 25 µl after addition of sterile distilled water, and a PCR reaction was carried out. The PCR reaction was performed under the following conditions: after initial denaturation at 95° C. for 10 minute, 40 cycles of thermal denaturation at 95° C. for 1 minute, annealing at 55° C. for 1 minute, extension reaction at 72° C. for 2 minute, and final extension reaction at 72° C. for 5 minutes. The sense primer and antisense primer used for the reaction are as follows:

A sense primer of positions 21 to 38 of SEQ ID NO:2 and an antisense primer of the positions 1323 to 1342 of SEQ ID NO:2; and A sense primer of the positions 21 to 38 of SEQ ID NO:4 and an antisense primer of the positions 712 to 731 of SEQ ID NO:4.

(3) The obtained RT-PCR solution with molecular weight marker (100 bp ladder: manufactured by Fermentas Inc.) was electrophoresed on agarose gel (1% Agarose S: manufactured by Nippon Gene Co., Ltd.) in TAE buffer and visualized in an ethidium bromide solution. The PCR products were collected from the gel and purified by the commercially-available kit (QIAquick Gel Extraction Kit: manufactured by Qiagen, Inc.). 50 ng of the obtained PCR products and 25 ng of TA cloning vector (pT7BlueT vector: manufactured by Novagen, Co.) were mixed with 3 μl of T4DNA ligase solution (solution I of DNA ligation kit Ver II: manufactured by Takara Shuzo Co., Ltd.), and the mixture solution was subjected to ligation at 16° C. for 2 hours.

(4) By the same method as that described in Example 2, plasmid DNA was prepared, the base sequence was determined, and obtained were plasmids into which cDNA of the positions 21 to 1342 of SEQ ID NO:2 and cDNA of the positions 21 to 731 of SEQ ID NO:4 were cloned.

(5) Construction of DR3 Expression Vector With a Tag

To 2 μg of the obtained plasmid into which cDNA at the positions 21 to 1342 of SEQ ID NO:2 was cloned were added 5units of BamHI (manufactured by Takara Shuzo Co., Ltd.), 5units of XbaI (manufactured by Takara Shuzo Co., Ltd.), and 1.25 μl of 10×K buffer (manufactured by Takara Shuzo Co., Ltd.). The mixture solution had a total volume of 25 μl after addition of sterile distilled water. After incubation at 37° C. for 4 hours, the reaction solution with molecular weight marker (1 kbp ladder: manufactured by Fermentas Inc.) was electrophoresed on agarose gel (1% Agarose S: manufactured by Nippon Gene Co., Ltd.) in TAE buffer. Approximately 1.3 kbp of DNA band was collected from the gel and purified by the commercially-available kit (QIAquick Gel Extraction Kit: manufactured by Qiagen, Inc.).

(6) To 2 μg of pcDNA3.1/His vector (product name: manufactured by Invitrogen Corp.) were added 5 units of BamHI (manufactured by Takara Shuzo Co., Ltd.), 5 units of XbaI (manufactured by Takara Shuzo Co., Ltd.), and 1.25 μl of 10×K buffer (manufactured by Takara Shuzo Co., Ltd.). The mixture solution had a total volume of 25 μl after addition of sterile distilled water. After incubation at 37° C. for 4 hours, the reaction solution with molecular weight marker (1 kbp ladder: manufactured by Fermentas Inc.) was electrophoresed on agarose gel (1% Agarose S: manufactured by Nippon Gene Co., Ltd.) in TAE buffer. Approximately 5.5 kbp of DNA band was collected from the gel and purified by the commercially-available kit (QIAquick Gel Extraction Kit: manufactured by Qiagen, Inc.).

(7) 30 ng of DNA fragments purified in Reference Example 1 (5) and 30 ng of pcDNA3.1/His vector purified in Reference Example 1 (6) were mixed with 4 μl of T4DNA ligase solution (solution I of DNA ligation kit Ver II: manufactured by Takara Shuzo Co., Ltd.), and the mixture was subjected to ligation at 16° C. for 2 hours.

(8) By the same method as that in Example 2, plasmid DNA was prepared, and expression vector with an Xpress tag, in which the position 21 to 1342 of SEQ ID NO:2 was recombined.

(9) To 2 μg of the plasmid, obtained in Reference Example 1(4), in which cDNA of the position 21 to 1342 of SEQ ID NO:2 was cloned were added 5 units of Sal I (manufactured by Takara Shuzo Co., Ltd.), 5 units of EcoR I (manufactured by Takara Shuzo Co., Ltd.), and 2.5 μl of 10×H buffer (manufactured by Takara Shuzo Co., Ltd.). The mixture solution had a total volume of 25 μl after addition of sterile distilled water. After incubation at 37° C. for 4 hours, the reaction solution with molecular weight marker (1 kbp ladder: manufactured by Fermentas Inc.) was electrophoresed on agarose gel (1% Agarose S: manufactured by Nippon Gene Co., Ltd.) in TAE buffer. Approximately 1.3 kbp of DNA band was collected from the gel and purified by the commercially-available kit (QIAquick Gel Extraction Kit: manufactured by Qiagen, Inc.).

(10) 2 μg of pEGEP-C2 vector (product name: Clontech) was digested with Sal I and EcoR I as in Reference Example 1(9), and 4.7 kbp of DNA band was collected from the gel and purified by the commercially-available kit (QIAquick Gel Extraction Kit: manufactured by Qiagen, Inc.).

(11) 30 ng of DNA fragments purified in Reference Example 1(9) and 30 ng of pEGEP-C2 vector purified in Reference Example 1(10) were mixed with 4 μl of T4DNA ligase solution (solution I of DNA ligation kit Ver II: manufactured by Takara Shuzo Co., Ltd.), and the mixture was subjected to ligation at 16° C. for 2 hours.

(12) By the same method as that in Example 2, plasmid DNA was prepared, and constructed expression vector with an EGFP (Enhanced green fluorescent protein) tag, in which the positions 21 to 1342 of SEQ ID NO:2 was recombined.

(13) To 2 μg of the obtained plasmid in Reference Example 1(4), in which cDNA of the position 21 to 731 of SEQ ID NO:3 was cloned were added 5 units of Sal I (manufactured by Takara Shuzo Co., Ltd.) and 4 μl of 10×H buffer (manufactured by Takara Shuzo Co., Ltd.). The mixture solution had a total volume of 40 μl after addition of sterile distilled water. After incubation at 37° C. for 4 hours, the reaction solution was removed protein with phenol chloroform (1:1) solution, and plasmid was collected by ethanol precipitation. To the obtained plasmid were added 5 units of BamHI (manufactured by Takara Shuzo Co., Ltd.) and 4 μl of 10×K buffer (manufactured by Takara Shuzo Co., Ltd.). The mixture solution had a total volume of 40 μl after addition of sterile distilled water. After incubation at 37° C. for 4 hours, the reaction solution with molecular weight marker (100 bp ladder: manufactured by New England Biolabs (NEB) Co.) was electrophoresed on agarose gel (1% Agarose S: manufactured by Nippon Gene Co., Ltd.) in TAE buffer. Approximately 0.8 kbp of DNA band was collected from the gel and purified by the commercially-available kit (QIAquick Gel Extraction Kit: manufactured by Qiagen, Inc.).

(14) 2 μg of pEGEP-C1 vector (product name: Clontech) was digested with Sal I and BamH I as in Reference Example 1(13), and 4.7 kbp of DNA band was collected from the gel and purified by the commercially-available kit (QIAquick Gel Extraction Kit: manufactured by Qiagen, Inc.).

(15) 30 ng of DNA fragments purified in Reference Example 1(13) and 30 ng of pEGEP-C1 vector purified in Reference Example 1(14) were mixed with 4 μl of T4DNA ligase solution (solution I of DNA ligation kit Ver II: manufactured by Takara Shuzo Co., Ltd.), and the mixture was subjected to ligation at 16° C. for 2 hours.

(16) By the same method as that in Example 2, plasmid DNA was prepared, and constructed expression vector with an EGFP tag, in which the positions 21 to 731 of SEQ ID NO:4 was recombined.

(17) As by the method in Example 6(1) and (2), the introduction of the mutation was performed to a plasmid that was obtained by cloning cDNA at positions 21 to 1342 of SEQ ID NO:2 and cDNA at the positions 21 to 731 of SEQ ID NO:4, which were obtained in Reference Example 1(4).

The base to which the mutation was introduced was the 564th base of SEQ ID NO:4 or 2 (corresponding to position 1755 of SEQ ID NO:1), and this base was substituted from A to G. By the introduction of the mutation, Asp at the 159th base was substituted by Gly in each protein. Note that the primer set used here is shown below.

```
Sense primer:
5'-TGTTCCCGCAGAGGTACTGACTGTGGGA-3'    (SEQ ID NO:8)

Antisense primer:
5'-TCCCACAGTCAGTACCTCTGCGGGAACA-3'    (SEQ ID NO:19)
```

(18) Using the obtained plasmid, by the same method as that described in Reference Example 1(9) to (12), constructed were expression vectors with an EGFP tag in which the positions 21 to 1342 having the A to G mutation at the position 564 of SEQ ID NO:2 were recombined. Further, by the same method as that described in Reference Example 1(13) to (16), constructed were expression vectors with an EGFP tag in which positions 21 to 731 having the A to G mutation at position 564 of SEQ ID NO:4 were recombined.

Hereinafter, these expression vectors with the tags will be referred to as follows:

Vector A: Expression vector with an Xpress tag in which the positions 21 to 1342 of SEQ ID NO:2 were recombined;

Vector B: Expression vector with an EGFP tag in which the positions 21 to 1342 of SEQ ID NO:2 were recombined;

Vector C: Expression vector with an EGFP tag in which the positions 21 to 1342 having the A to G mutation at the position 564 of SEQ ID NO:2 were recombined;

Vector D: Expression vector with an EGFP tag in which the positions 21 to 731 of SEQ ID NO:4 were recombined, and Vector E: Expression vector with an EGFP tag in which the positions 21 to 731 having the A to G mutation at the position 564 of SEQ ID NO:4 were recombined.

(19) On the previous day of the transfection, 293T cells suspended in DMEM/10% FCS were inoculated by $2\times10^5$ on a plate having six-wells. Transfection was performed by lipofection method using LipofectAMINE Plus Reagent (manufactured by Gibco-BRL). 0.5 µg of Vector A and Vectors B, C, D, and E, each having 0.5 µg were mixed, and 6 µl of LipofectAMINE Reagent (plus reagent: manufactured by Gibco-BRL) was added to the mixture. The mixture had a total volume of 100 µl with DMEM and allowed to stand at room temperature for 15 minutes. 4 µl of LipofectAMINE Reagent (product name: manufactured by Gibco-BRL) and 96 µl of DMEM were added to the solution. After further allowed to stand at room temperature for 15 minutes, the total volume of the solution was 1 ml with 800 µl of DMEM. The solution was added to the cells on the plate, whose supernatants were removed, and cultured at 37° C. in 5% of $CO_2$ for 3 hours. To the solution whose supernatant was removed was added 3 ml of DMEM/10% FCS. After further cultivation for 48 hours, cells were collected. After being washed in PBS, the obtained cells were suspended in 250 µl of solubilization buffer and fragmentized by supersonic waves. The cell-fragmentized solution was centrifuged at 15000 rpm for 10 minutes and its supernatant was provided as cell-solubilized solution for an experiment.

(20) To 200 µl of the obtained cell-solubilized solution was added 300 µl of solubilization buffer and further added 25 µl of protein A-agarose solution (manufactured by Roche). The mixture was mixed by inversion at 4° C. for four hours. The solution was centrifuged at 12000 rpm for 20 seconds. To the collected supernatant was added 1 µg of anti-GFP antibody (manufactured by Santa Cruz Biotechnology), and the mixture was mixed by inversion at 4° C. for two hours. To this solution was added 25 µl of protein A-agarose solution (manufactured by Roche), and the mixture was mixed by inversion at 4° C. overnight. The solution was centrifuged at 12000 rpm for 20 seconds, and its supernatant was removed. Thereafter, for washing, its precipitate was suspended in 500 µl of solubilization buffer and mixed by inversion at 4° C. for 20 minutes. After this washing operation being repeated three times, the precipitate was suspended in 30 µl of 2× sample buffer and heated at 95° C. for five minutes. The resultants were samples of SDS-polyacrylamide gel electrophoresis (PAGE).

(21) 20 µl of the obtained samples with protein marker (pre-stained marker, broad: manufactured by APRO Life Science Institute, Inc.) was subjected to usual SDS-PAGE on 7.5% SDS-PAGE gel. After the electrophoresis, protein was subjected to transfer to PVDF membrane (manufactured by Millipore, Co.) by semi-dry-type blotting apparatus. Used for transfer buffer were 100 mM tris, 192 mM glycine, and 10% methanol.

(22) The PVDF membrane on which protein was transferred was immersed into TBS solution containing 5% of skimmed milk and shaken at room temperature for 1 hour. Next, the PVDF membrane was immersed into the solution in which 1/1000 (content ratio to solvent) of anti-Xpress antibody (manufactured by Invitrogen Corp.) was added to TBS solution and reacted at room temperature overnight. After being washed in TBS solution containing 0.05% Tween-20 three times each for 10 minutes, the PVDF membrane was immersed into the solution in which 1/1000 (content ratio to solvent) of HRP labeled anti-mouse IgG antibody (manufactured by Amersham Pharmacia Biotech Ltd.) was added to TBS solution containing 0.1% Tween-20, and reacted at room temperature for two hours. After being washed in TBS solution containing 0.1% Tween-20 three times each for 10 minutes, the PVDF membrane was immersed into detection reagent (ECL system: manufactured by Amersham Pharmacia Biotech Ltd.) and subjected to exposure to X-ray film.

Figure 5:
FIG. 5 is an X-ray photograph showing a result of western blotting with anti-Xpress antibody after immunoprecipitation with anti-GFP antibody.

The result is shown in FIG. 5. All of the proteins expressed from the vectors B, C, D, and E were proved to bind to the protein expressed from the vector A. More specifically, it became clear that the normal DR3 protein formed a complex not only with the normal protein but also with the mutant proteins expressed from the vectors C, D, and E.

REFERENCE EXAMPLE 2

The Effect of Mutant DR3 in the Binding of Normal DR3 and TRADD (1) Preparation of TRADD cDNA To 0.5 µl of cDNA solution (human testis Marathon-Ready cDNA: product name, manufactured by Clontech) were added 2.51 µl of 10×LA buffer (product name: manufactured by Takara Shuzo Co., Ltd.), 2.5 µl of 25 mM magnesium chloride, 4 µl of 2.5 mM deoxynucleotide mixture, 0.25 µl of 20M sense primer, 0.25 µl of 20 µM antisense primer, and 1.25U DNA polymerase reagent (LA Taq DNA polymerase: manufactured by Takara Shuzo Co., Ltd.). The mixture solution had a total volume of 25 µl after addition of sterile distilled water, and a PCR reaction was carried out. The PCR reaction was performed under the following conditions: after initial denaturation at 95° C. for 1 minute, 35 cycles of thermal denaturation at 95° C. for 1 minute, annealing at 62° C. for 1 minute, extension reaction at 72° C. for 1 minute, and final extension reaction at 72° C. for 5 minutes. The primers used for the reaction are shown below.

```
Sense primer:
5'-CGAGGCGGCCAGGAGGTG-3'        (SEQ ID NO:20)

Antisense primer:
5'-GGTTCAGCAATAGCCGCAGA-3'      (SEQ ID NO:21)
```

(2) The obtained solution with molecular weight marker (100 bp ladder: manufactured by Fermentas Inc.) was electrophoresed on agarose gel (1% Agarose S: manufactured by Nippon Gene Co., Ltd.) in TAE buffer and visualized in an ethidium bromide solution. The PCR products were collected from the gel and purified by the commercially-available kit (QIAquick Gel Extraction Kit: manufactured by Qiagen, Inc.). 25 ng of the obtained PCR products and 25 ng of TA cloning vector (pT7BlueT vector: manufactured by Novagen, Co.) were mixed with 2.5 μl of T4DNA ligase solution (solution I of DNA ligation kit Ver II: manufactured by Takara Shuzo Co., Ltd.), and the mixture solution was subjected to ligation at 16° C. for 1 hour.

(3) By the same method as that described in Example 2, plasmid DNA was prepared, the base sequence was determined, and plasmids into which TRADD cDNA was cloned were obtained.

(4) Construction of TRADD Expression Vector with Tag

To 2 μg of the plasmid in which TRADD cDNA was cloned, which was obtained in Reference Example 2(3), were added 5 units of EcoR I (manufactured by Takara Shuzo Co., Ltd.), 5 units of Sal I (manufactured by Takara Shuzo Co., Ltd.), and 3 μl of 10×H buffer (manufactured by Takara Shuzo Co., Ltd.). The mixture solution had a total volume of 30 μl after addition of sterile distilled water. After incubation at 37° C. for 4 hours, the reaction solution with molecular weight marker (1 kbp ladder: manufactured by Fermentas Inc.) was electrophoresed on agarose gel (1% Agarose S: manufactured by Nippon Gene Co., Ltd.) in TAE buffer. Approximately 1 kbp of DNA band was collected from the gel and purified by the commercially-available kit (QIAquick Gel Extraction Kit: manufactured by Qiagen, Inc.).

(5) To 1 μg of pCMV-Tag2 vector (product name: Stratagene, Co.) were added 5 units of EcoR I (manufactured by Takara Shuzo Co., Ltd.), 5 units of Sal I (manufactured by Takara Shuzo Co., Ltd.), and 3 μl of 10×H buffer (manufactured by Takara Shuzo Co., Ltd.). The mixture solution had a total volume of 30 μl after addition of sterile distilled water. After incubation at 37° C. for 4 hours, the reaction solution with molecular weight marker (1 kbp ladder: manufactured by Fermentas Inc.) was electrophoresed on agarose gel (1% Agarose S: manufactured by Nippon Gene Co., Ltd.) in TAE buffer. 4.3 kbp of DNA band was collected from the gel and purified by the commercially-available kit (QIAquick Gel Extraction Kit: manufactured by Qiagen, Inc.).

(6) 30 ng of DNA fragments purified in Reference Example 2(4) and 30 ng of pCMV-Tag2 vector purified in Reference Example 2(5) were mixed with 2.5 μl of T4DNA ligase solution (solution I of DNA ligation kit Ver II: manufactured by Takara Shuzo Co., Ltd.), and the mixture was subjected to ligation at 16° C. for 2 hours.

(7) By the same method as that in Example 2, plasmid DNA was prepared, and constructed was TRADD expression vector with a Flag tag. Hereinafter, this vector will be referred to as vector F.

(8) On the previous day of the transfection, 293T cells suspended in DMEM/10% FCS were inoculated by 2×10$^5$ on a plate having six-wells. Transfection was performed by lipofection method using LipofectAMINE Reagent manufactured by Gibco-BRL. The combinations of vectors were given as follows.

1. 0.2 μg of pcDNA3.1/His C (product name: Invitrogen Corp.), 0.1 μg of vector F
2. 0.2 μg of Vector A, 0.1 μg of Vector F
3. 0.2 μg of Vector A, 0.1 μg of Vector E, 0.1 μg of Vector F
4. 0.2 μg of Vector A, 0.2 μg of Vector E, 0.1 μg of Vector F The vectors A and E are the vectors shown in Reference Example 1, and the vector A has a His tag, in addition to the Xpress tag. Note that, the total volume of the vector was 1 μg by pcDNA3.1 (product name: Invitrogen Corp.). 61 μl of LipofectAMINE Reagent (plus reagent: manufactured by Gibco-BRL) was added to the combinations 1 to 4. The mixture had a total volume of 100 μl with DMEM and allowed to stand at room temperature for 15 minutes. 4 μl of LipofectAMINE Reagent (manufactured by Gibco-BRL) and 96 μl of DMEM were added to the solution. After further allowed to stand at room temperature for 15 minutes, the total volume of the solution had 1 ml with 800 μl of DMEM. The solution was added to the cells on the plate, whose supernatants were removed, and cultured at 37° C. in 5% of $CO_2$ for 3 hours. To the solution whose supernatant was removed was added 3 ml of DMEM/10% FCS. After further cultivation for 24 hours, cells were collected. After being washed in PBS, the obtained cells were suspended in 250 μl of solubilization buffer and fragmentized by supersonic waves. The cell-fragmentized solution was centrifuged at 15000 rpm for 10 minutes and its supernatant was provided as cell-solubilized solution for an experiment.

(9) Solubilization buffer was added to 100 μg of the cell-solubilized solution so that the total volume of the solution was 500 μl. Further, 25 μl of protein A-agarose solution (manufactured by Roche) was added to the mixture solution. The mixture was mixed by inversion at 4° C. for four hours. The solution was centrifuged at 12000 rpm for 20 seconds. To the collected supernatant was added 1 μg of anti-HisG antibody (product name: manufactured by Invitrogen, Corp.), and the mixture was mixed by inversion at 4° C. for two hours. To this solution was added 25 μl of protein A-agarose solution, and the mixture was mixed by inversion at 4° C. overnight. The solution was centrifuged at 12000 rpm for 20 seconds, and its supernatant was removed. Thereafter, for washing, its precipitate was suspended in 500 μl of solubilization buffer and mixed by inversion at 4° C. for 20 minutes. After this washing operation repeated twice, a similar washing was further performed twice with 500 μl of washing buffer, and washing with 500 μl of solubilization buffer was finally performed again. The precipitate was suspended in 30 μl of 2× sample buffer and heated at 95° C. for five minutes. The resultants were samples of SDS-polyacrylamide gel electrophoresis (PAGE).

(10) 20 μl of the obtained sample with protein marker (pre-stained marker, broad: manufactured by APRO Life Science Institute, Inc.) was subjected to usual SDS-PAGE on 9% SDS-PAGE gel. After the electrophoresis, a protein was subjected to transfer to PVDF membrane by semi-dry-type blotting apparatus. Used for transfer buffer were 100 mM tris, 192 mM glycine, and 10% methanol.

(11) The PVDF membrane on which the protein was transferred was immersed into TBS solution containing 5% of skimmed milk and shaken at room temperature for 1 hour. Next, the PVDF membrane was immersed into the solution in which 1/1000 (content ratio to solvent) of anti-Flag antibody (manufactured by Sigma Chemical Company) was added to TBS solution and reacted at room temperature for 30 minutes. After being washed in TBS solution three times each for 1 to 2 minutes, the PVDF membrane was immersed into the solution in which 1/1000 (content ratio to solvent) of HRP labeled anti-mouse IgG antibody (manufactured by Amersham Pharmacia Biotech Ltd.) was added to TBS solution, and reacted at room temperature for 30 minutes. After being washed in TBS solution three times each for 15 minutes, the PVDF membrane was immersed into detection reagent (ECL system: manufactured by Amersham Pharmacia Biotech Ltd.) and subjected to exposure to X-ray film.

Figure 6:
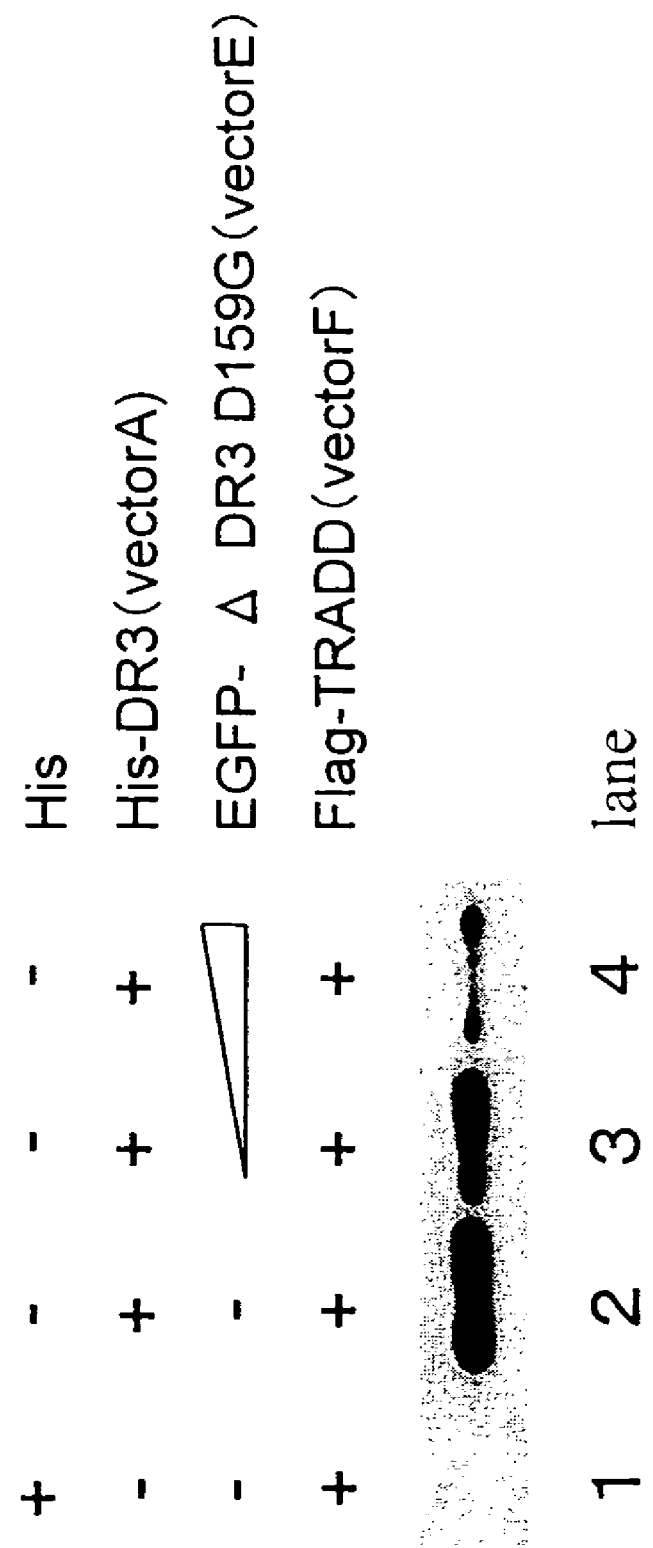
FIG. 6 is an X-ray photograph showing a result of western blotting with anti-Flag antibody after immunoprecipitation with anti-His antibody.

The result is shown in FIG. 6. When the normal DR3 and the mutant DR3 were expressed simultaneously, the volume of TRADD bound to the normal DR3 reduced with the volume of the mutant DR3 (lanes 3 and 4). In other words, the mutant DR3 inhibited the binding of the normal DR3 and TRADD.

REFERENCE EXAMPLE 3

Expression of Caspase-8 in Peripheral-blood Mononuclear Cell (1) 10 ml of peripheral blood drawn using heparin each from five RA patients and four healthy subjects is mixed with the equivalent volume of PBS, and the reaction mixture was overlaid upon 20 ml of Lymphoprep (Daiichi Pure Chemicals Co., Ltd.). After centrifugation at 1500 rpm for 30 minutes, the layer of peripheral-blood mononuclear cells were collected and washed in PBS. The cells were suspended in a culture medium (RPM11640/10% FCS) so as to be $5\times10^5$ cells/ml. 10 ml of the cell suspension was sprayed on a 10 cm plate and cultured at 37° C. in 5% of $CO_2$ for 48 hours, with or without stimulation by 20 ng/ml of PMA (Sigma Chemical Company) and 1 µg/ml of PHA (Difco Laboratories). After the collected cells were washed in PBS, the cells were suspended in solubilization buffer 150 µl and incubated on ice for 30 minutes. The solution was centrifuged at 15000 rpm for 10 minutes, and collected supernatant was provided for cell solubilization solution.

(2) 10 µg of the obtained cell solubilization solution with protein marker (pre-stained marker, broad: manufactured by APRO Life Science Institute, Inc.) was subjected to usual SDS-PAGE on 7.5% SDS-PAGE gel. After the electrophoresis, a protein was subjected to transfer to PVDF membrane (manufactured by Millipore, Co.) by semi-dry-type blotting apparatus. Used for transfer buffer were 100 mM tris, 192 mM glycine, and 10% methanol.

(3) The PVDF membrane on which the protein was transferred was immersed into TBS-T solution containing 5% of skimmed milk and shaken at room temperature for 1 hour. Next, the PVDF membrane was immersed into the solution in which 1/1000 (content ratio to solvent) of anti-caspase-8 antibody (manufactured by Medical & Biological Laboratories, Co., Ltd.) was added to TBS-T solution containing 1% of skimmed milk and reacted at 4° C. overnight. After being washed in TBS-T solution three times each for 10 minutes, the PVDF membrane was immersed into the solution in which 1/1000 (content ratio to solvent) of HRP labeled anti-mouse IgG antibody (manufactured by Amersham Pharmacia Biotech Ltd.) was added to TBS-T solution, and reacted at room temperature for 1 hour. After being washed in TBS-T solution three times each for 10 minutes, the PVDF membrane was immersed into detection reagent (ECL system: manufactured by Amersham Pharmacia Biotech Ltd.) and subjected to exposure to X-ray film.

Band density of caspase-8/a and caspase-8/b are converted into numeral forms by NIH Image soft, and the result was shown in the form of relative values obtained by dividing the values under the stimulation of PMA and PHA by the values without no stimulation and a result was shown. The result in the form of average value ± standard deviation is shown as follows:

Healthy subjects: 0.72±0.19, and

RA patients: 1.33±0.23.

Because of the stimulation of cells, in the healthy subjects, observed was the decrease of caspase-8 (caspase-8/a and caspase-8/b), i.e. degradation of caspase-8. In the RA patients, the degradation of caspase-8 was not observed.

EXAMPLE 10

Induction of Cell Death by the Supplement of Normal DR3

(1) Construction of Normal DR3 Expression Vector

To 2 µg of the plasmid, obtained in Reference Example 1(4), into which the positions 21 to 1342 of SEQ ID NO:2 were cloned were added 5 units of BamHI (manufactured by Takara Shuzo Co., Ltd.), 5 units of XbaI (manufactured by Takara Shuzo Co., Ltd.), and 1.25 µl of 10×K buffer (manufactured by Takara Shuzo Co., Ltd.). The mixture solution had a total volume of 25 µl after addition of sterile distilled water. After incubation at 37° C. for 4 hours, the reaction solution with molecular weight marker (1 kbp ladder: manufactured by Fermentas Inc.) was electrophoresed on agarose gel (1% Agarose S: manufactured by Nippon Gene Co., Ltd.) in TAE buffer. Approximately 1.3 kbp of DNA band was collected from the gel and purified by the commercially-available kit (QIAquick Gel Extraction Kit: manufactured by Qiagen, Inc .).

(2) To 2 µg of pcDNA3.1 (product name: manufactured by Invitrogen Corp.) were added 5 units of BamHI (manufactured by Takara Shuzo Co., Ltd.), 5 units of XbaI (manufactured by Takara Shuzo Co., Ltd.), and 1.25 µl of 10×K buffer (manufactured by Takara Shuzo Co., Ltd.). The mixture solution had a total volume of 25 µl after addition of sterile distilled water. After heated at 37° C. for 4 hours, the reaction solution with molecular weight marker (1 kbp ladder: manufactured by Fermentas Inc.) was electrophoresed on agarose gel (1% Agarose S: manufactured by Nippon Gene Co., Ltd.) in TAE buffer. 5.6 kbp of DNA band was collected from the gel and purified by the commercially-available kit (QIAquick Gel Extraction Kit: manufactured by Qiagen, Inc.).

(3) 30 ng of DNA fragments purified in Example 10(1) and 30 ng of pcDNA3.1 vector purified in Example 10(2) were mixed with 4 µl of T4DNA ligase solution (solution I of DNA ligation kit Ver II: manufactured by Takara Shuzo Co., Ltd.), and the mixture was subjected to ligation at 16° C. for 2 hours.

(4) By the same method as that in Example 2, plasmid DNA was prepared, and constructed was normal DR3 expression vector, in which the position 21 to 1342 of SEQ ID NO:2 was recombined.

(5) Construction of Mutant DR3 Expression Vector

To 2 μg of the plasmid, obtained in Reference Example 1(17), into which the positions 21 to 731 of SEQ ID NO:4 having the A to G mutation at the position 564 of SEQ ID NO:3 were cloned were added 5 units of EcoRI (manufactured by Takara Shuzo Co., Ltd.), 5 units of HindIII (manufactured by Takara Shuzo Co., Ltd.), and 4 μl of 10×M buffer (manufactured by Takara Shuzo Co., Ltd.). The mixture solution had a total volume of 40 μl after addition of sterile distilled water. After incubation at 37° C. for 4 hours, the reaction solution with molecular weight marker (100 bp ladder: New England Biolabs (NEB) Co.) was electrophoresed on agarose gel (1% Agarose S: manufactured by Nippon Gene Co., Ltd.) in TAE buffer. Approximately 0.8 kbp of DNA band was collected from the gel and purified by the commercially-available kit (QIAquick Gel Extraction Kit: manufactured by Qiagen, Inc.).

(6) 2 μg of pcDNA3.1/V5-His (product name: Invitrogen Corp.) was digested with EcoRI and HindIII as in Example 10(5), and 5.5 kbp of DNA band was collected from the gel and purified by the commercially-available kit (QIAquick Gel Extraction Kit: manufactured by Qiagen, Inc.).

(7) 30 ng of DNA fragments purified in Example 10(5) and 30 ng of pcDNA3.1/V5-His vector purified in Example 10(6) were mixed with 4 μl of T4DNA ligase solution (solution I of DNA ligation kit Ver II: manufactured by Takara Shuzo Co., Ltd.), and the mixture was subjected to ligation at 16° C. for 2 hours.

(8) By the same method as that in Example 2, plasmid DNA was prepared, and constructed was mutant DR3 expression vectors, in which the positions 21 to 731 of SEQ ID NO:4 having the A to G mutation at the position 564 of SEQ ID NO:3 was recombined.

(9) 4 μg of the normal vector or mutant vector with 1 μg of pRL-TK vector (product name: manufactured by Promega) were subjected to Jurkat cells. Note that, the total volume of the vector was 11 μg with control vector (pcDNA3.1, product name: manufactured by Invitrogen Corp.). After being subjected to electroshock, the mixture was allowed to stand still on ice for 10 minutes, and the total volume of the mixture was 4 ml with RPMI1640/10% FCS. The mixture was cultured at 37° C. on 6 well plate in 5% $CO_2$ for 24 hours. After the collected cells were washed in phosphate buffered saline, the cells were solubilized in 100 μl of cell lysis solution (Passive Lysis Buffer: manufactured by Promega). 20 μl of this solution was mixed with 50 μl of luciferase substrate (Stop & Glo substrate: manufactured by Promega), and the mixture was subjected to the measurement in the amount of luminescence using luminometer (Luminoskan: manufactured by Dainippon Pharmaceutical Co., Ltd.)

In the cells in which pRL-TK vector is transfected, a luciferase gene is translated, so that its cell lysis solution causes chemiluminescence. On the other hand, it is considered that when apoptosis was inducted by the expression of DR3, the decrease in the number of cells reduces the amount of luminescence. More specifically, this experiment is to detect the induction of cell death using an index of the amount of luminescence.

The amount of luminescence in the cell lysis solution to which control vectors (pcDNA3.1) were introduced was defined to be 100, and the amounts of luminescence in the cell lysis solution to which the vectors were introduced were shown by relative values. The results were as follows:

Normal DR3: 11.1;

Mutant DR3: 101.7, and

Normal DR3+Mutant DR3: 10.3.

Regarding the cell to which the mutant DR3 was transfected, the amount of luminescence represented a substantially equivalent value to that of the cell to which the control vector was transfected. More specifically, apoptosis was not induced to this cell. On the other hand, regarding the cell to which the equal volumes of the normal DR3 and mutant DR3 were transfected, the amount of luminescence represented a low value as that of the cell to which only the normal DR3 was introduced, and the cell death was inducted. Thus, the supplement of the normal DR3 is considered to be useful for a therapeutic method for RA.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICATION OF THE PRESENT INVENTION

The present invention relates to a genome and proteins having mutations, a method of diagnosis of human rheumatoid arthritis by using the mutations of the genome and proteins (in other words, a method of evaluating (determining) the onset or the onset possibility thereof), a diagnostic kit for detecting the mutations, and a therapeutic method and remedies for rheumatoid arthritis. The present invention is useful because it enables diagnosis of the onset or the onset possibility of rheumatoid arthritis to be performed both easily and surely and at high accuracy. Furthermore, the present invention is useful in providing new prevention methods, therapeutic methods, and remedies for rheumatoid arthritis.

What is claimed is:

1. A purified nucleic acid associated with rheumatoid arthritis comprising the nucleotide sequence of SEQ ID NO:1 having the following mutation:
   an adenine (A) to thymine (T) substitution at position 2678.

2. A method of evaluating onset or onset possibility of rheumatoid arthritis in a human subject, comprising the step of detecting in a human subject a nucleic acid associated with rheumatoid arthritis comprising the nucleotide sequence of SEQ ID NO:1 having the following mutation:
   an adenine (A) to thymine (T) substitution at position 2678, wherein detection of said nucleic acid is indicative of the possibility of the onset of rheumatoid arthritis in the subject.

3. A method of evaluating onset or onset possibility of rheumatoid arthritis in a human subject, comprising the step of detecting in a human subject the presence of a mutation in a nucleic acid associated with rheumatoid arthritis wherein the nucleic acid comprises the nucleotide sequence of SEQ ID NO:1, and wherein said mutation is an adenine (A) to thymine (T) substitution at position 2678 in SEQ ID NO:1, wherein the presence of the mutation in the nucleic acid is indicative of the possibility of the onset of rheumatoid arthritis in the subject.

4. A kit for evaluating the onset or onset possibility of rheumatoid arthritis in a human subject, the kit comprising a reagent comprising the nucleotide sequence of SEQ ID NO:1 having an adenine (A) to thymine (T) substitution at position 2678; or a nucleic acid fully complementary to said nucleotide sequence of SEQ ID NO:1 having the adenine (A) to thymine (T) substitution at position 2678.

* * * * *